(12) United States Patent
Akassoglou

(10) Patent No.: US 8,569,242 B2
(45) Date of Patent: Oct. 29, 2013

(54) METHOD OF TREATING DEGENERATIVE DISORDERS OF THE NERVOUS SYSTEM

(75) Inventor: Katerina Akassoglou, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/337,504

(22) Filed: Dec. 27, 2011

(65) Prior Publication Data

US 2012/0093812 A1    Apr. 19, 2012

Related U.S. Application Data

(60) Continuation of application No. 12/896,410, filed on Oct. 1, 2010, now abandoned, which is a division of application No. 12/067,792, filed as application No. PCT/US2006/037211 on Sep. 25, 2006, now Pat. No. 7,807,645.

(60) Provisional application No. 60/702,218, filed on Sep. 23, 2005.

(51) Int. Cl.
- *A01N 37/18* (2006.01)
- *A61K 39/395* (2006.01)
- *C07K 16/00* (2006.01)

(52) U.S. Cl.
USPC ..... 514/17.8; 514/17.7; 514/17.9; 530/388.1; 530/388.15; 530/388.25

(58) Field of Classification Search
None
See application file for complete search history.

(56) References Cited

U.S. PATENT DOCUMENTS

| | | | |
|---|---|---|---|
| 4,455,290 A | 6/1984 | Olexa et al. | |
| 5,372,933 A | 12/1994 | Zamarron et al. | |
| 5,599,790 A * | 2/1997 | Altieri et al. | 514/13.6 |
| 5,877,295 A | 3/1999 | Diamond | |
| 6,086,876 A | 7/2000 | Karp | |
| 7,544,655 B2 | 6/2009 | Marx | |
| 7,807,645 B2 | 10/2010 | Akassoglou | |
| 2003/0031675 A1 | 2/2003 | Mikesell | |
| 2004/0136994 A1 | 7/2004 | Kelsall | |
| 2008/0226652 A1 | 9/2008 | Bakker | |
| 2009/0098117 A1 | 4/2009 | Ferrara | |
| 2009/0221507 A1 | 9/2009 | Akassoglou | |

FOREIGN PATENT DOCUMENTS

| | | |
|---|---|---|
| WO | 2007024817 | 3/2007 |
| WO | 2007048186 | 5/2007 |

OTHER PUBLICATIONS

Adams et al., 2004, Mol. Interventions, 4(3):163-176.
Akassaglou et al., 2002, Neuron, 33:861-875.
Altieri et al., 1993, "The structural motif glycine 190-valine 202 of the fibrinogen gamma chain interacts with CD11b/CD18 integrin (alpha M beta 2, Mac-1) and promotes leukocyte adhesion," The Journal of Biological Chemistry, 268 (3):1847-1853.
Hu et al., 2002, "Molecular basis of biomaterial-mediated foreign body reactions," [Erratum to document CA136:284361], Blood, 99(11):3908.
Hu et al., 2001, "Molecular basis of biomaterial-mediated foreign body reactions," Blood, 98(4):1231-1238.
Ugarova et al., 1998, "Identification of a novel recognition sequence for integrin alphaMbeta2 within the y-chain of fibrinogen,"Journal of Biological Chemistry, 273(35):22519-22527.
Ugarova et al., 2003, "Sequence y377-395(P2), but not y190-202(P1), is the binding site for the alphaMI-domain of integrin alphaMbeta2 in the yC-domain of fibrinogen," Biochemistry, 42:9365-9373.
Yakubenko et al, 2001, "Identification of the binding site for fibrinogen recognition peptide y-383-395 within the alphaMI-domain of integrin alphaMbeta2," Journal of Biologic Chemistry, 276(17):13995-14003.

* cited by examiner

*Primary Examiner* — Olga N Chernyshev
(74) *Attorney, Agent, or Firm* — Sutherland Asbill & Brennan LLP

(57) ABSTRACT

The invention herein related to methods and compositions for treating nervous system disorders. The methods comprise administration of antibodies directed towards peptides that bind to receptors important in disease progression, thus attenuating the disease.

9 Claims, 47 Drawing Sheets

US 8,569,242 B2

METHOD OF TREATING DEGENERATIVE DISORDERS OF THE NERVOUS SYSTEM

CROSS REFERENCES TO RELATED APPLICATIONS

This application is a continuation of U.S. application Ser. No. 12/896,410 filed Oct. 1, 2010, abandoned, which is a divisional of U.S. application Ser. No. 12/067,792, filed Mar. 21, 2008, issued as U.S. Pat. No. 7,807,645, which is a U.S. National Phase of PCT/US2006/037211 filed Sep. 25, 2006 which claims priority from U.S. Provisional Application No. 60/720,218 filed on Sep. 23, 2005, each of which is incorporated herein by reference in its entirety.

STATEMENT OF GOVERNMENT INTEREST

The invention was made with government support under NS52189 awarded by the National Institutes of Health. The government has certain rights in the invention.

STATEMENT REGARDING FEDERALLY SPONSORED RESEARCH OR DEVELOPMENT

This invention was made in part with Government support under NIH Grant No. NS52189. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 23, 2011, is named 24978012.txt and is 1,671 bytes in size.

FIELD

The present teachings relate to methods and compositions for treatment of neuronal disorders.

INTRODUCTION

Degenerative neuronal disorders such as multiple sclerosis (MS) can involve inflammatory demyelination and autoimmune responses. Microglia, in particular perivascular microglia, are believed to be necessary not only for the maintenance, but also for the onset of inflammatory demyelination in central nervous system (CNS) autoimmune disease (3). Activation of microglia contributes to both neuronal (46) and oligodendrocyte death (31) via release of cytokines and nitric oxide. In MS, inflammatory processes are associated with destruction of myelin sheaths, and can also involve axonal damage that can lead to permanent functional deficits, such as paralysis and loss of vision (1). Resident microglia are considered responsible for the effector mechanism leading to demyelination, via their ability to phagocytose myelin and secrete proinflammatory cytokines (2). However, mechanisms of perivascular microglia activation in inflammatory demyelination have not been identified.

In MS lesions, perivascular activation of microglia colocalizes with areas of blood brain barrier (BBB) disruption (5). Magnetic resonance imaging (MRI) studies link BBB breakdown with clinical relapse (6). Moreover, in vivo imaging studies have shown that BBB disruption provokes the immediate and focal activation of microglia (7).

One of the earliest events coupled to BBB disruption in MS is leakage of the blood protein fibrinogen in the nervous system that results in perivascular deposition of fibrin (8-11). Although fibrinogen has been primarily studied for its functions in blood coagulation, accumulating evidence has identified pivotal roles for fibrinogen in inflammation (12, 13) and infection (14, 15). Fibrinogen is a classic acute-phase reactant, characterized by a unique molecular structure with binding sites for cellular receptors that regulate the inflammatory process (16, 17). Research in MS animal models such as Experimental Allergic Encephalitis (EAE) in mice shows that prophylactic fibrin depletion either by genetic depletion of fibrinogen (18) or by prophylactic administration of anticoagulants (18, 19) ameliorates disease pathogenesis. However, the use of anticoagulants are potentially limited in therapeutic value, due to the hemorrhagic side effects of fibrin-depleting agents. Fibrinogen is not present in the healthy CNS, but only leaks in the brain after BBB disruption, thus serving as an environmental "danger" signal (4).

Recent evidence has shown that paralysis of CD11b-positive microglia ameliorates inflammatory demyelination in the presence of peripheral. T-cells and macrophages (3). CD11b is the alpha chain of the CD11b/CD18 integrin receptor (other names: Mac-1, $\alpha_M\beta_2$, Complement Receptor 3) that in inflammatory demyelination regulates phagocytosis of myelin (21, 22). Myelin phagocytosis is thought to be subjected to modulation between inactive and active states of the Mac-1 receptor (23). Immobilized fibrinogen and insoluble fibrin, but not soluble fibrinogen, have been identified as physiological, high-affinity ligands for Mac-1 (15, 24, 25). Interestingly, in MS lesions fibrin deposition colocalizes with areas of activated microglia (11).

SUMMARY

The present inventors have developed methods for treating degenerative disorders of the nervous system. These methods comprise administering to a mammalian subject such as a human patient in need of treatment, a therapeutically effective amount of a composition comprising a peptide consisting essentially of about 19 amino acids and having at least about 90% sequence identity with the peptide sequence tyr-ser-met-lys-lys-thr-thr-met-lys-ile-ile-pro-phe-asn-arg-leu-thr-ile-gly (YSMKKTTMKIIPFNRLTIG) (SEQ ID NO: 1).

Some aspects of the invention include compositions for the treatment of a degenerative disorder of the nervous system. The compositions comprise a peptide consisting essentially of about 19 amino acids and having at least about 90% sequence identity with the amino acid sequence YSMKKTT-MKIIPFNRLTIG (SEQ ID NO: 1), and a pharmaceutically acceptable excipient.

In other aspects, the invention includes use of a peptide in the manufacture of a medicament for the treatment of a neurodegenerative disease, wherein the peptide consists essentially of about 19 amino acids and having at least about 90% sequence identity with the peptide sequence YSMKKTT-MKIIPFNRLTIG (SEQ ID NO: 1).

In yet other aspects, the invention includes methods of inhibiting microglia activation. These methods comprise contacting the microglia with a composition comprising a peptide consisting essentially of about 19 amino acids and having at least about 90% sequence identity with the peptide sequence YSMKKTTMKIIPFNRLTIG (SEQ ID NO: 1).

In yet other aspects, the invention includes methods of preventing development of a neurological disorder. These methods comprise administering to a subject an effective amount of a composition comprising a peptide consisting essentially of about 19 amino acids and having at least about 90% sequence identity with the peptide sequence tyr-ser-met-lys-lys-thr-thr-met-lys-ile-ile-pro-phe-asn-arg-leu-thr-ile-gly (YSMKKTTMKIIPFNRLTIG) (SEQ ID NO: 1).

In various configurations, the microglia can be microglia comprised by a mammalian subject, and the peptide can be comprised by a composition further comprising a pharmaceutically acceptable excipient.

In the various aspects and configurations of the invention, the peptide can consist essentially of the amino acid sequence YSMKKTTMKIIPFNRLTIG (SEQ ID NO: 1), or the peptide can consist of the sequence YSMKKTTMKIIPFNRLTIG (SEQ ID NO: 1).

In various aspects and configurations of the invention, the disease or disorder can be multiple sclerosis, spinal cord injury, stroke, or Alzheimer's Disease.

In one aspect, the peptide can be an isolated polypeptide comprising an amino acid sequence having at least about 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%; 97%, 98%, or 99% sequence identity to YSMKKTTMKIIPFNRLTIG (SEQ ID NO: 1).

These and other features, aspects and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

FIG. 1 illustrates IsoB4/DAPI immunostained microglia cultured on immobilized fibrinogen have increased cell body size adopting an amoeboid morphology (right column). Untreated primary microglia show small cell bodies and thin, bipolar processes (left column). LPS-treated cells show activated morphology characterized by cell body swelling (middle column). Top row shows antibody staining; middle row shows DAPI staining of nuclei; bottom row shows combined antibody and DAPI staining. Scale bar, 26 µm; inset, 21 µm.

Figure 4:
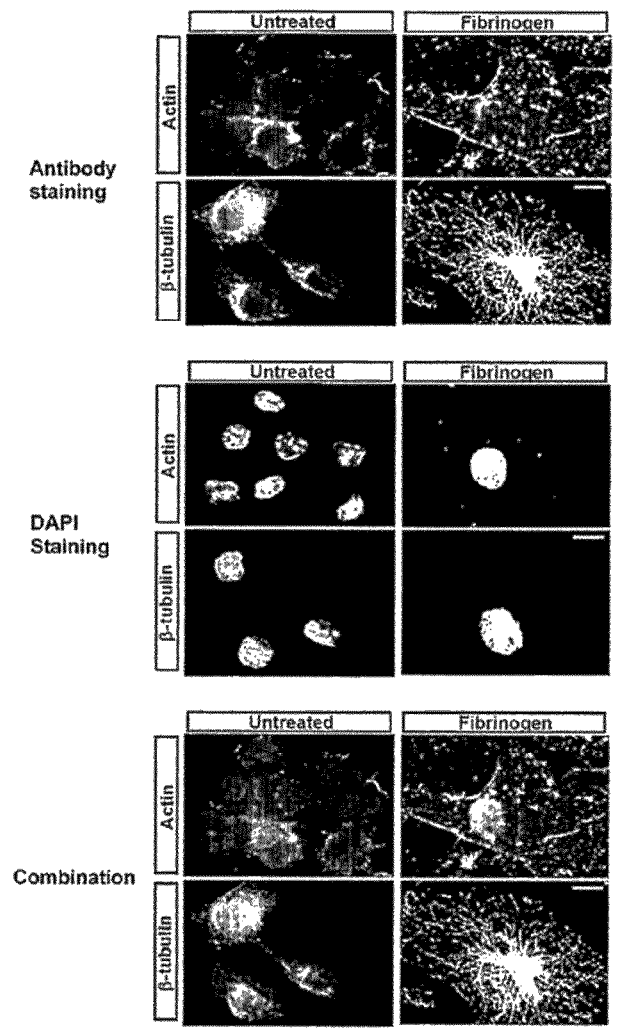

FIG. 4 depicts deconvolution microscopy of primary microglia revealed significant rearrangements of the cytoskeleton upon treatment with Fibrinogen. Microglia were stained with antibodies to actin and β-tubulin (top row) and the nucleus stained with DAPI (middle row). Bottom row shows combined antibody and DAPI staining. Scale bar, 4.4 µm.

Figure 5:
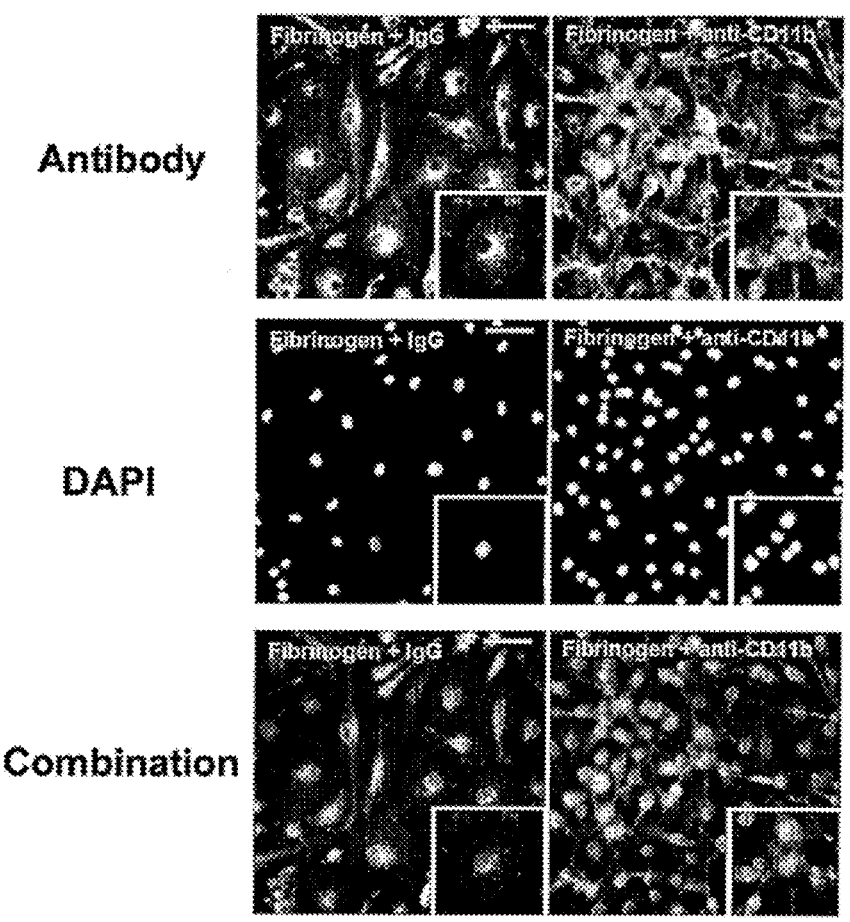

FIG. 5 depicts fibrinogen-induced morphologic activation of microglia blocked by the addition of a rat anti-CD11b neutralizing antibody (M1/70). Rat IgG (control) did not change the effects of fibrinogen in microglia activation. Top row shows antibody staining; middle row shows DAPI staining of nuclei; bottom row shows combined antibody and DAPI staining. Scale bar, 39 µm; inset, 17 µm.

Figure 6:
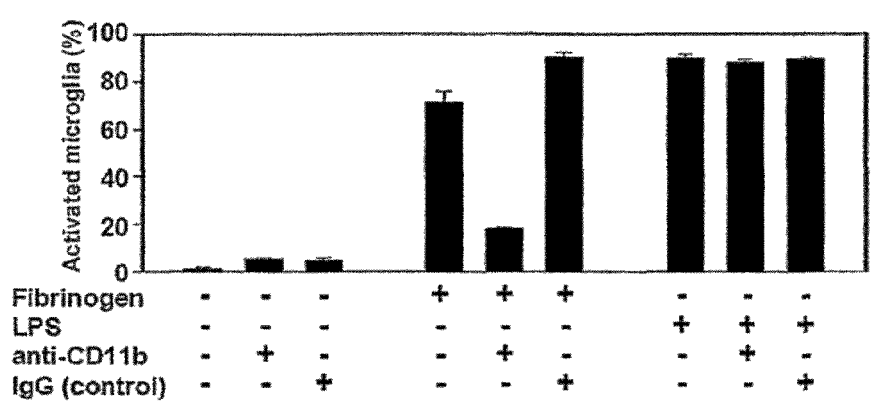

FIG. 6 depicts quantitation of microglia activation revealing that the Mac-1 neutralizing antibody blocks fibrinogen-induced activation but not LPS activation of microglia.

Figure 7:
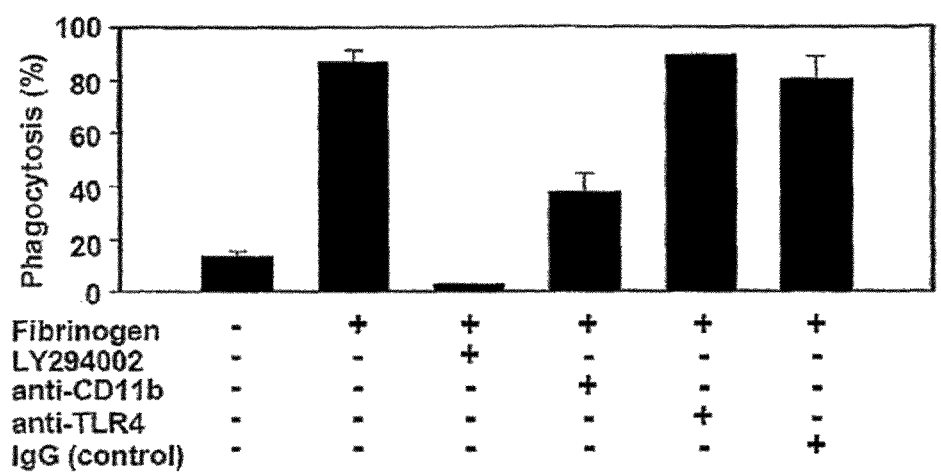

FIG. 7 depicts increased microglia phagocytosis upon fibrinogen stimulation blocked by the addition of a PI3K inhibitor (LY294002) and diminished in the presence of a CD11b neutralizing antibody. A control anti-TLR4 or IgG showed no reduction in fibrinogen stimulated phagocytosis.

Figure 8:
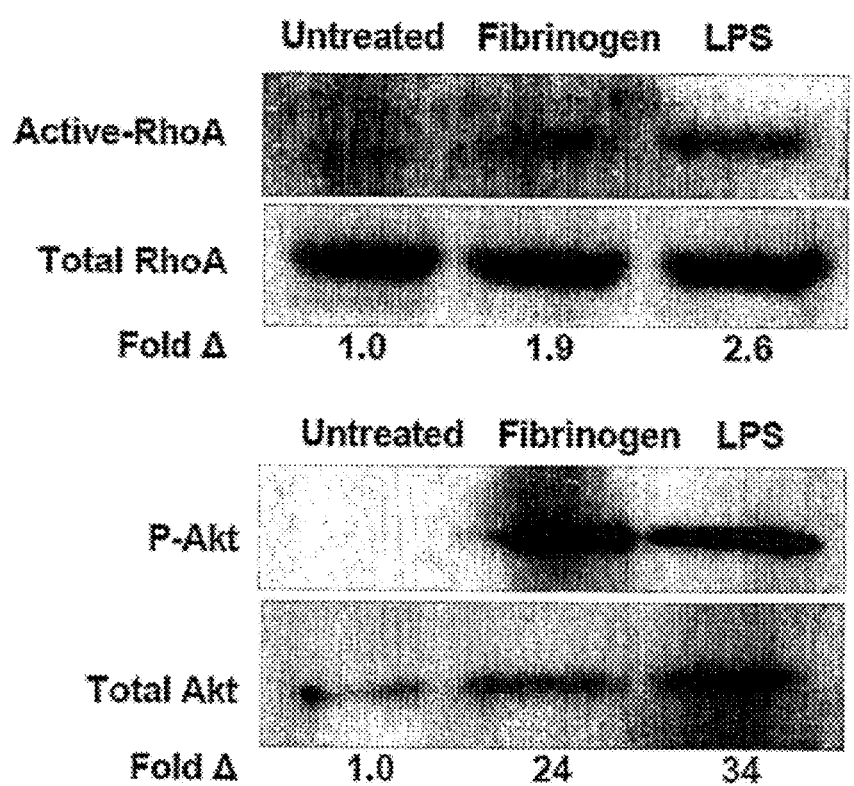

FIG. 8 depicts Western blots showing increased active RhoA and Akt activation upon fibrinogen stimulation of microglia. In both assays, LPS served as a positive control.

Figure 9:
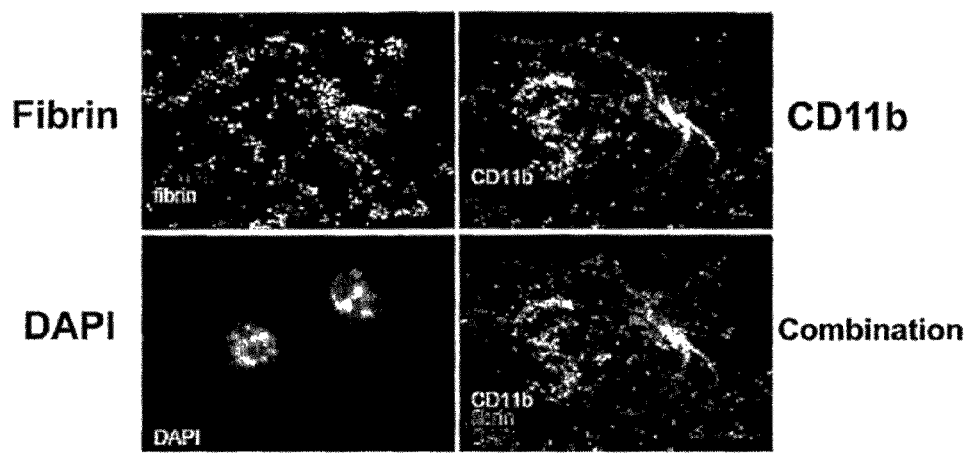

FIG. 9 depicts confocal microscopy demonstrating spatial interaction between CD11b-positive cells (top right) and fibrin (top left), DAPI staining (bottom left) and the combination (bottom right) in spinal cords from PLP139-151 immunized mice.

Figure 10:
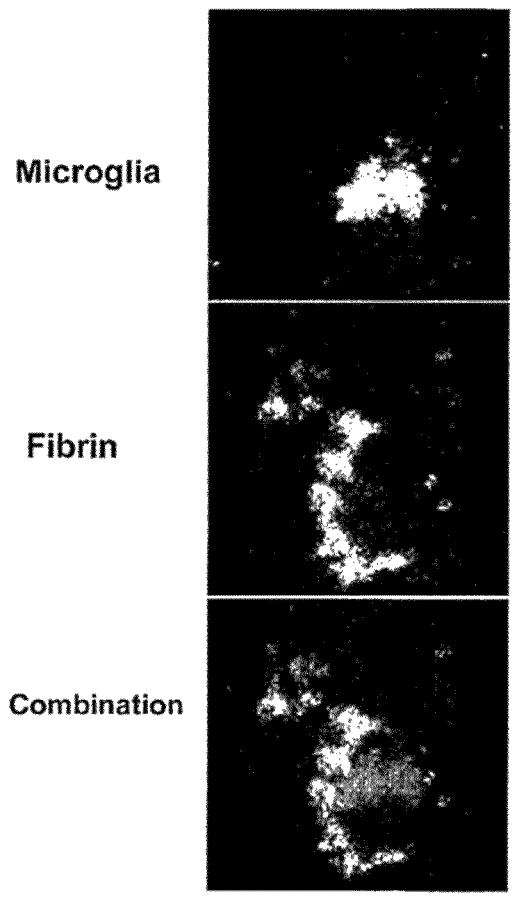

FIG. 10 depicts confocal double immunofluorescence showing fibrin (middle row) surrounding an activated microglia (top row) in a human early demyelinating plaque of acute MS. Bottom row shows combined antibody and DAPI staining. Scale bars, 6.7 µm, E; 15 µm, F.

Figure 11:
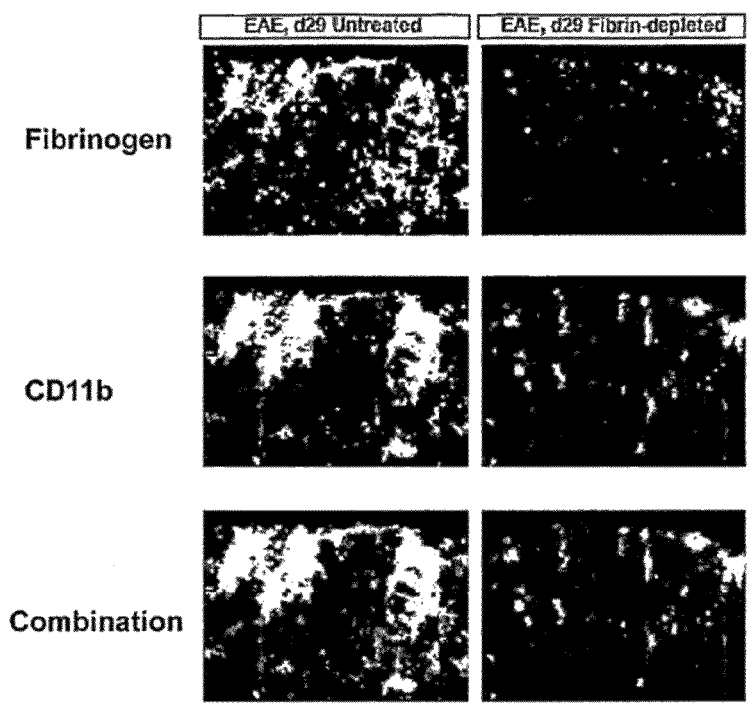
Figure 12:
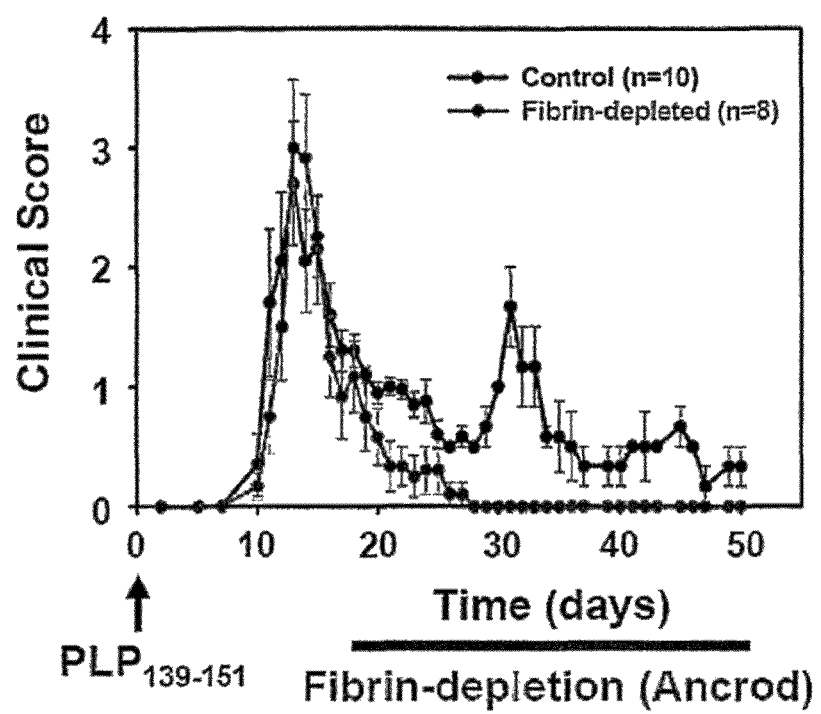

FIG. 11 depicts immunofluorescence of control (left panel) and fibrin-depleted (right panel) spinal cord with antibodies against fibrin(ogen) (top row) and CD11b (middle row). Activated CD11b positive cells colocalize with fibrin deposition in the control spinal cord (bottom row). Scale bar, 8.4 µm FIG. 12 depicts clinical scores of PLP139-151 immunized mice. Fibrin depletion begins after the first paralytic episode. Fibrin depleted mice (bottom curve, n=8) did not develop 1st or 2nd relapses as compared to control mice (upper curve, n=10).

Figure 13:
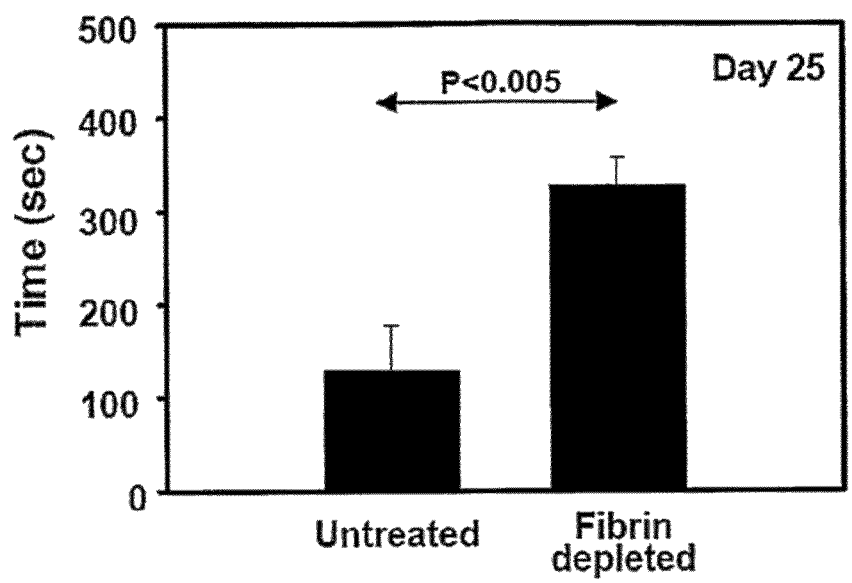

FIG. 13 depicts the results of a rotarod motor strength and coordination test. Fibrin-depleted mice outperformed control mice on day 25 postimmunization. Data are represented as the mean clinical score and are mean±SEM.

Figure 14:
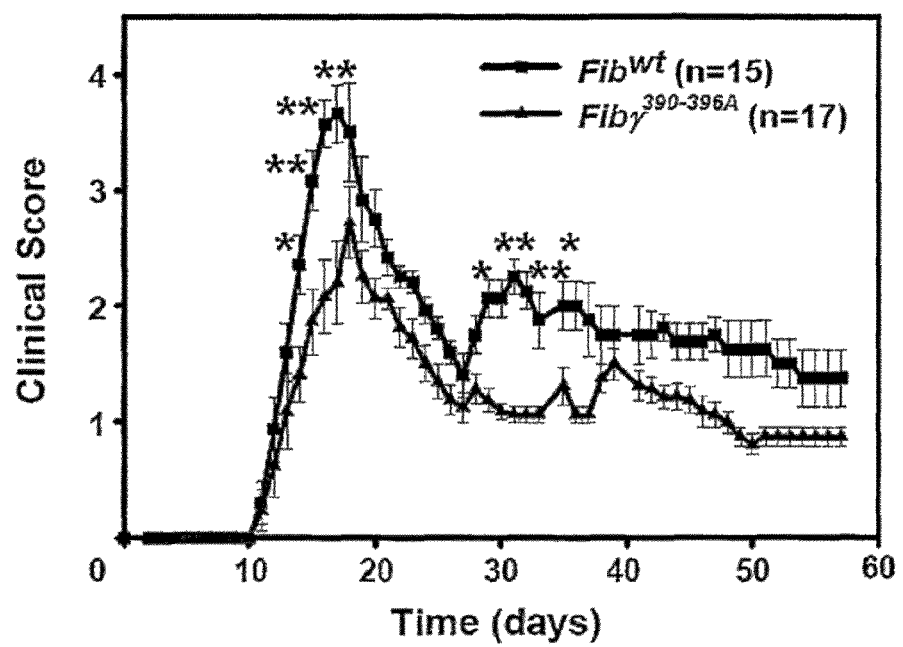

FIG. 14 depicts clinical scores of MOG35-55 immunized mice. Fibγ$^{390-396A}$ mice (triangles, n=17) show statistically significant lower clinical scores (*P<0.05, **P<0.01) than Fibγ$^{WT}$ control mice (squares, n=15).

Figure 15:
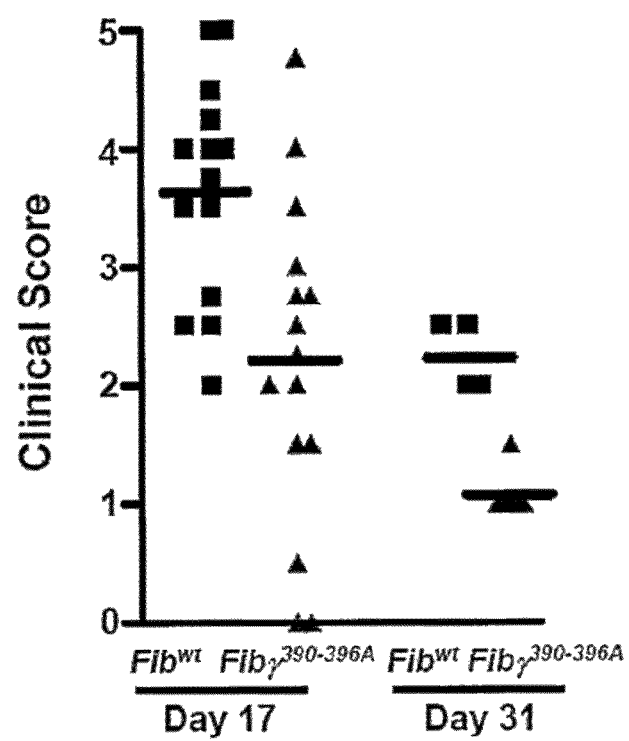

FIG. 15 depicts individual clinical scores from Fibγ$^{390-396A}$ and Fibγ$^{WT}$ mice on days 17 and 31 post-immunization.

Figure 16:
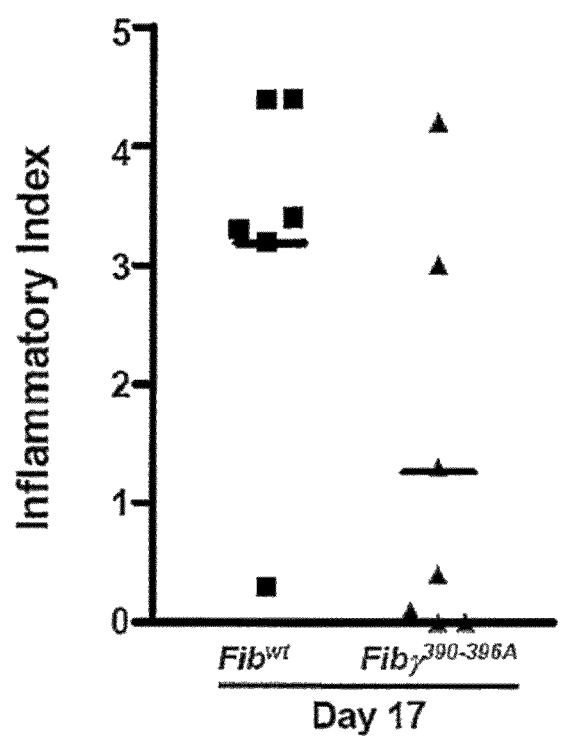

FIG. 16 depicts histological analysis of spinal cord sections revealed increased inflammation in the FibγWT mice versus the Fibγ$^{390-396A}$ mice.

Figure 17:
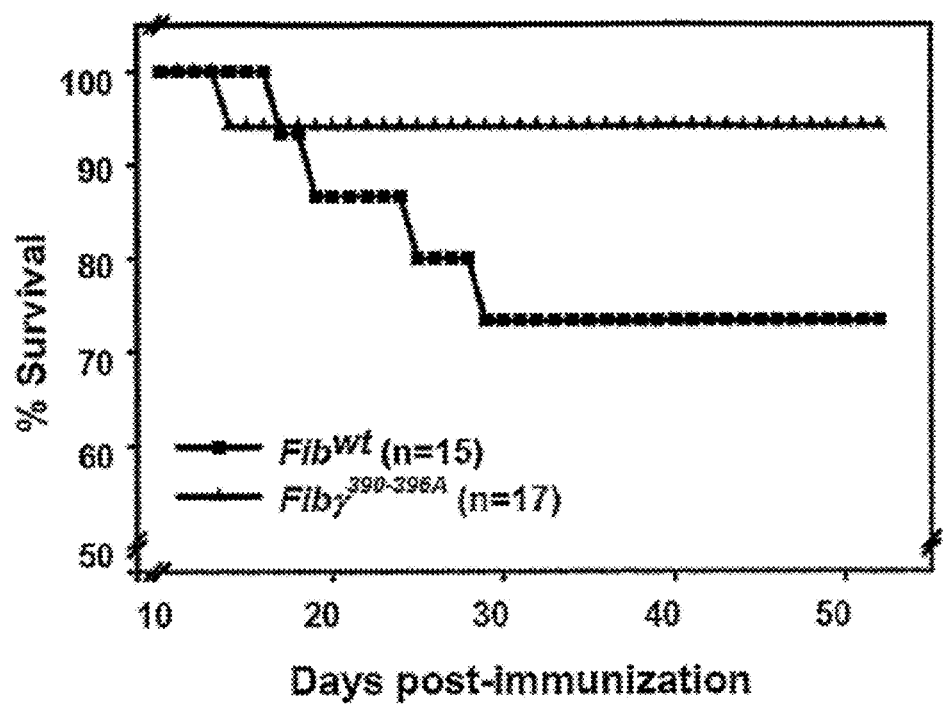

FIG. 17 depicts a survival curve of Fibγ$^{390-396A}$ and Fibγ$^{WT}$ mice after MOG35-55 immunization. Fibγ$^{390-396A}$ (upper curve) had a greater survival rate than the Fibγ$^{WT}$ mice (lower curve).

Figure 18:
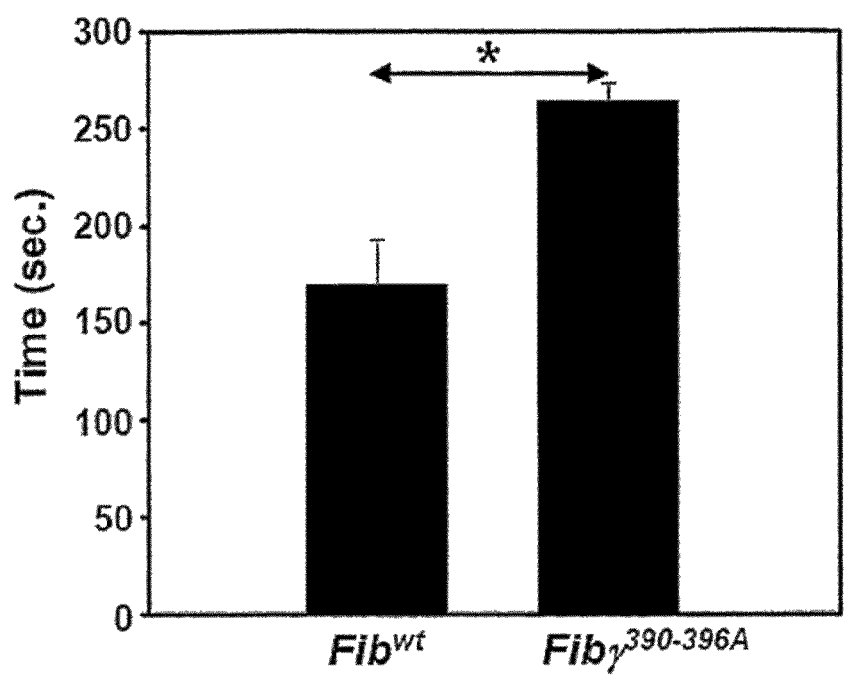

FIG. 18 depicts rotarod analysis of Fibγ$^{390-396A}$ and Fibγ$^{WT}$ mice on day 13 Fibγ$^{390-396A}$ significantly outperformed their wild-type counterparts in a behavioral test designed to assess motor skill function. (n=7 mice per group)

Figure 19:
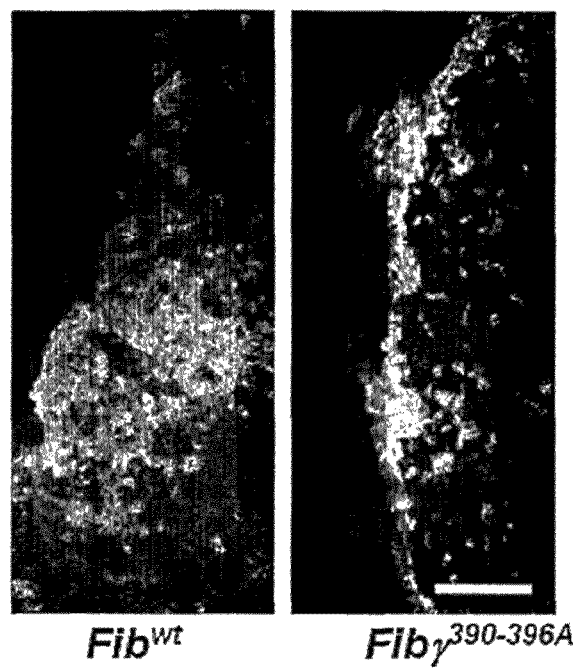

FIG. 19 depicts increased activation IsoB4 positive cells in Fibγ$^{WT}$ mice as compared to Fibγ$^{390-396}$ mice. Scale bar, 58 µm. *, P<0.05; **, P<0.01. Data are represented as the mean clinical score and are mean±SEM.

Figure 20:
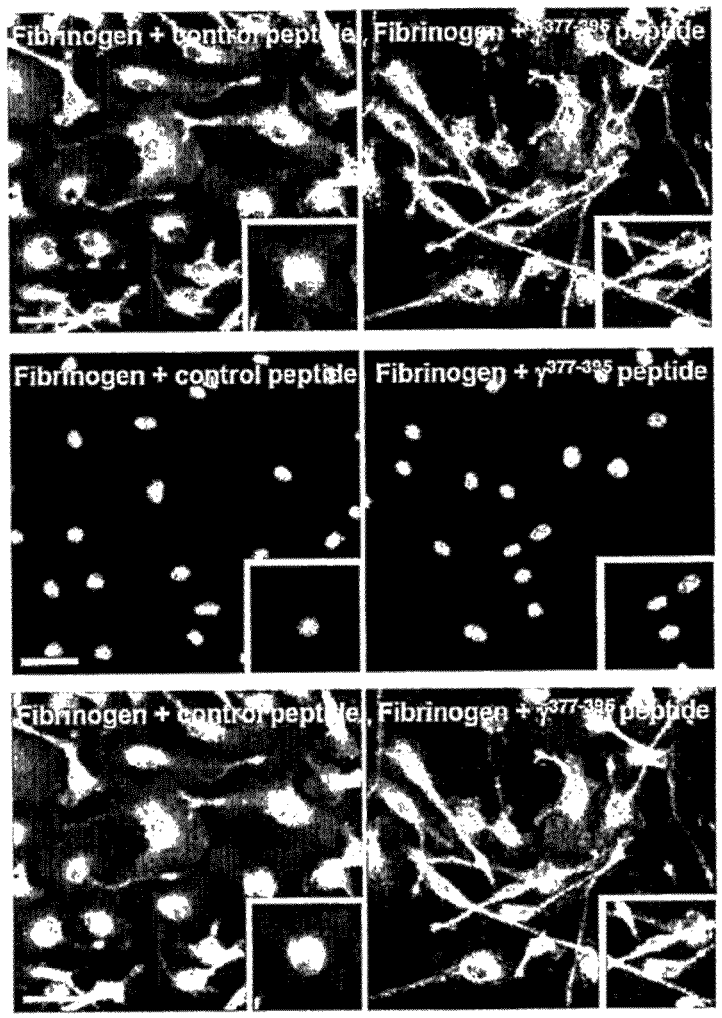

FIG. 20 depicts microglia activation upon fibrinogen stimulation is attenuated in the presence of γ$^{377-395}$. Top row shows antibody staining; middle row shows DAPI staining of nuclei; bottom row shows combined antibody and DAPI staining. Scale bar, 33 µm; inset, 29 µm.

Figure 21:
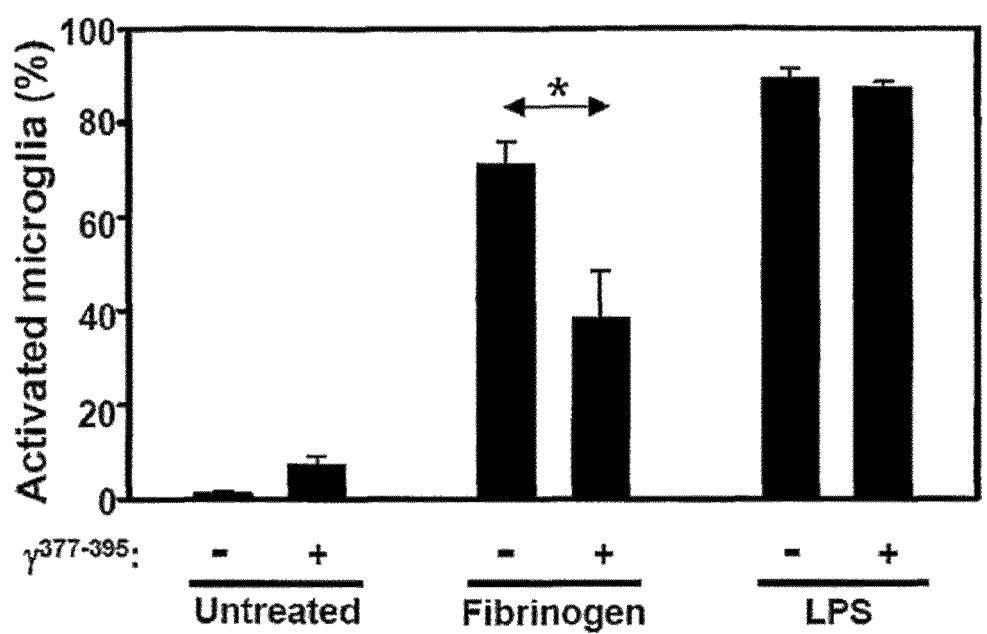

FIG. 21 depicts the quantitation of microglia activation reveals that γ$^{377-395}$ diminishes fibrinogen stimulated microglia activation but has no effect on LPS activation.

Figure 22:
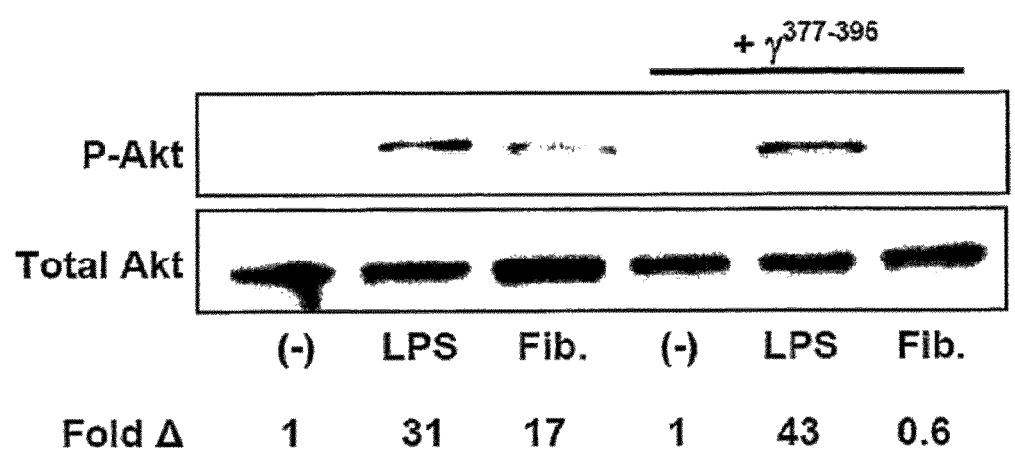

FIG. 22 shows that treatment of microglia with γ$^{377-395}$ blocks fibrinogen-induced Akt activation in vitro. LPS activation of Akt is unaffected by γ$^{377-395}$ treatment.

Figure 23:
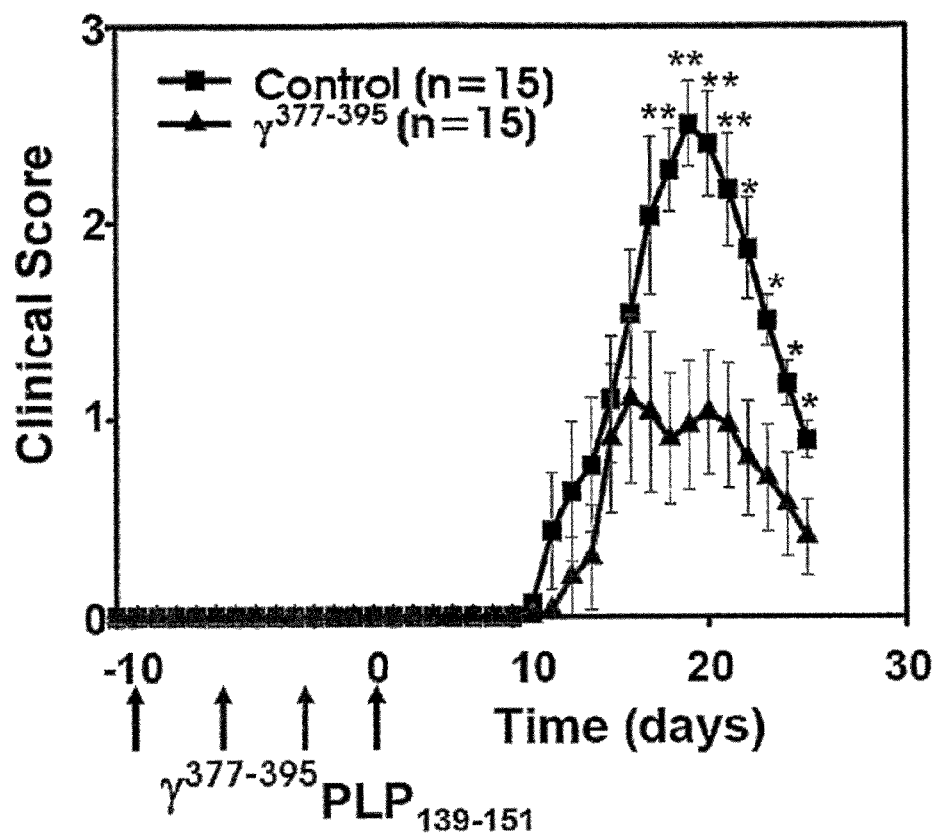

FIG. 23 depicts clinical scores from $\gamma^{377-395}$ peptide vaccinated mice. Mice were immunized with $\gamma^{377-395}$ peptide preceding EAE induction with PLP139-151 peptide. Vaccinated mice (triangles; n=15) had significantly reduced clinical scores, as compared to control mice (squares, n=15).

Figure 24:
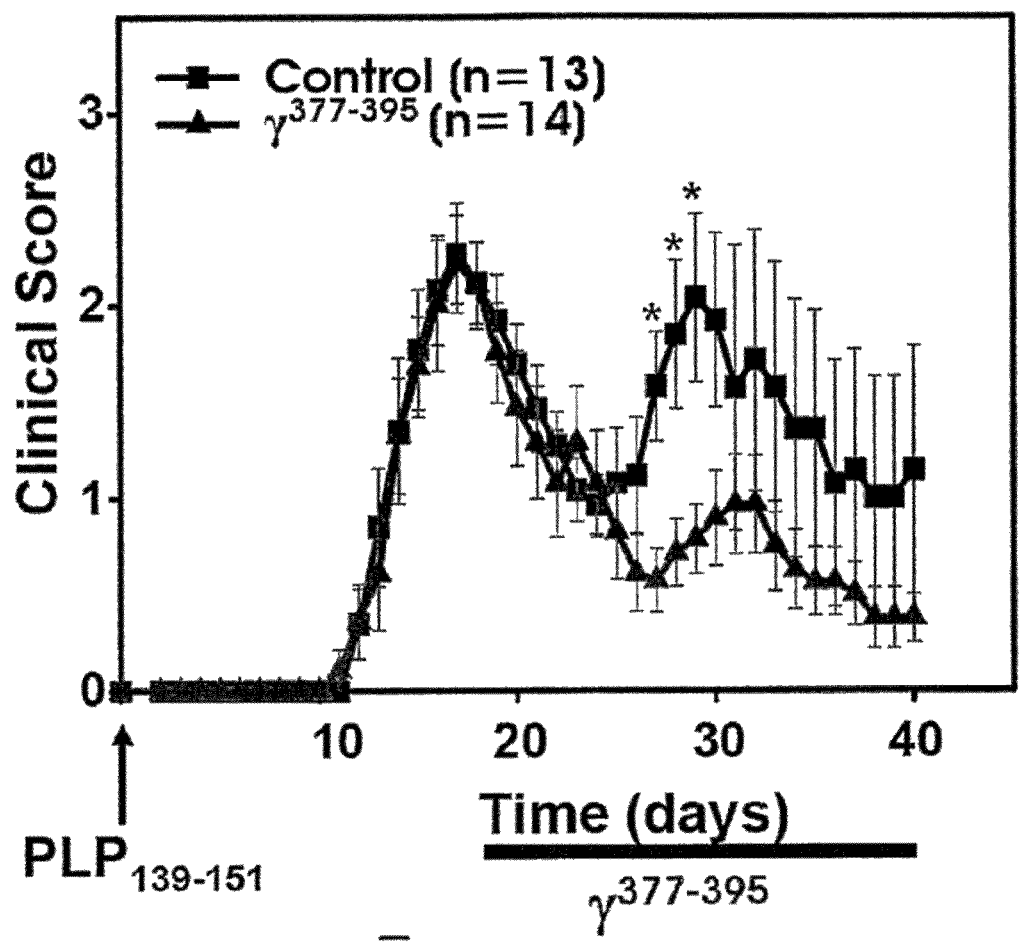

FIG. 24 depicts clinical scores from PLP139-151 immunized mice where the $\gamma^{377-395}$ peptide was administered every day intranasally after the peak of the initial paralytic episode $\gamma^{377-395}$ treated mice (triangles, n=14) did not show a relapse at approximately day 30 as compared to the controls (squares, n=13). *, P<0.05; ** P<0.01. Data are represented as the mean clinical score and are mean±SEM. Immunostaining for Mac-3 and iNOS on day 30 after immunization shows dramatic reduction of microglia activation in the $\gamma^{377-395}$ peptide-treated mice after EAE induction (FIG. 25), when compared to control (FIG. 26). Scale bar, 20 µm; Inset 10 µm.

Figure 25:
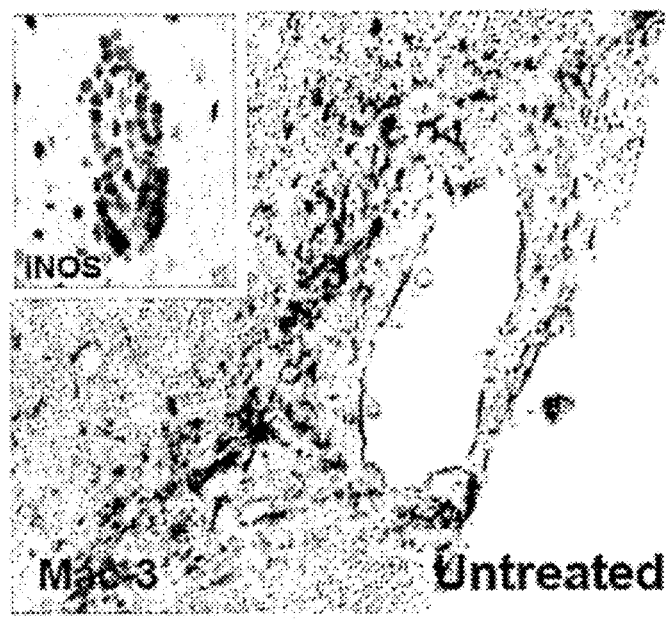
Figure 26:
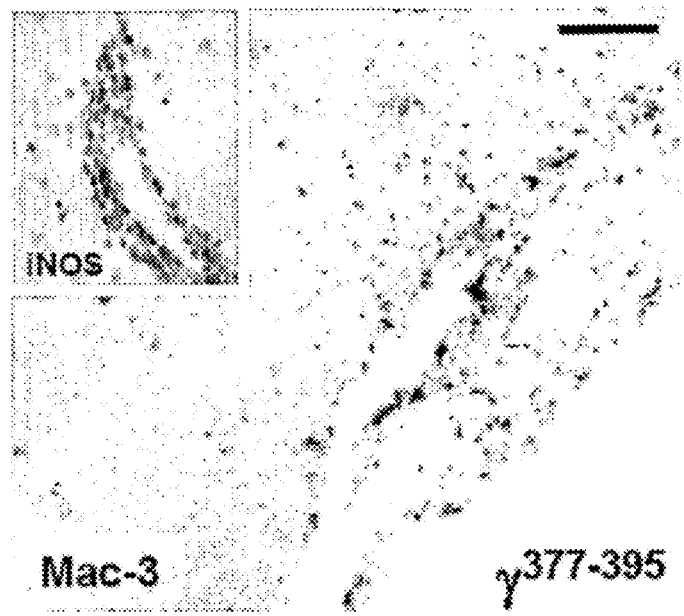

FIG. 25 shows dramatic reduction of microglia activation in the $\gamma^{377-395}$ peptide-treated mice after EAE induction when compared to FIG. 24. Scale bar, 20 µm; Inset 10 µm.

FIG. 26 shows a control for FIGS. 24 and 25. Scale bar, 20 µM; Inset 10 µm.

Figure 27:
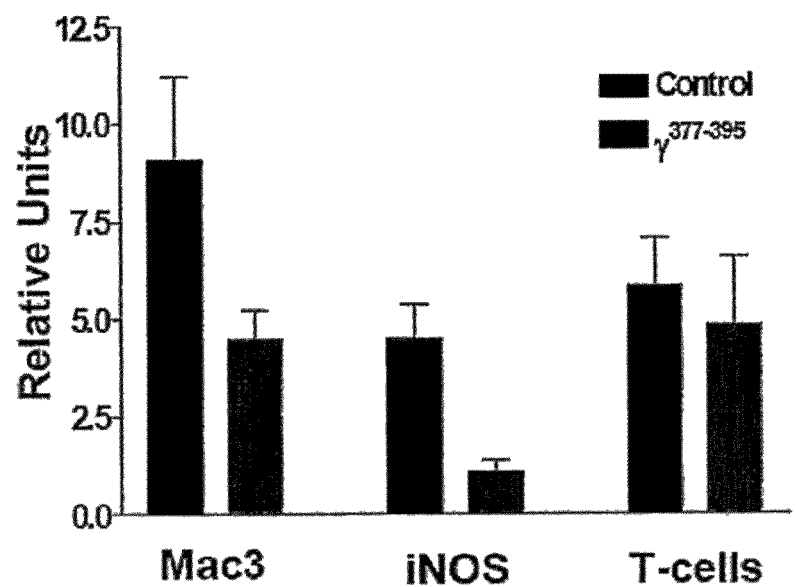

FIG. 27 depicts the quantitation showing a 2-fold reduction in Mac-3, a 4.2-fold reduction in iNOS after $\gamma^{377-395}$ peptide treatment, while there are no major differences in T cell infiltration.

Figure 28:
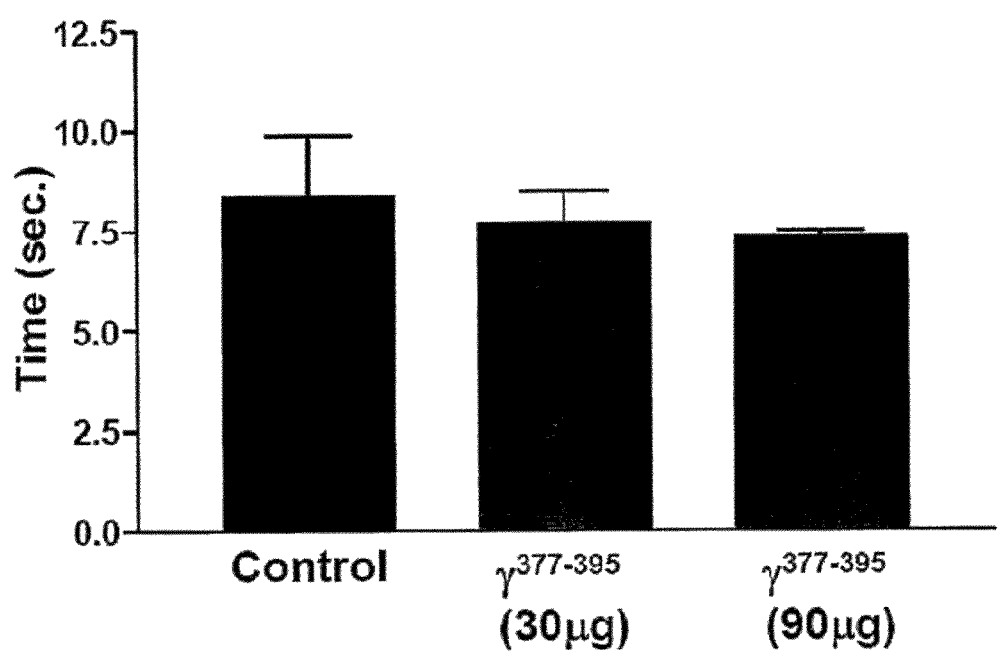

FIG. 28 depicts in vivo clotting time assayed in the presence of 30 µg of $\gamma^{377-395}$ peptide, the dose administered in vivo daily, and 90 µg of $\gamma^{377-395}$ peptide. Neither dose affected blood clotting times.

Figure 29:
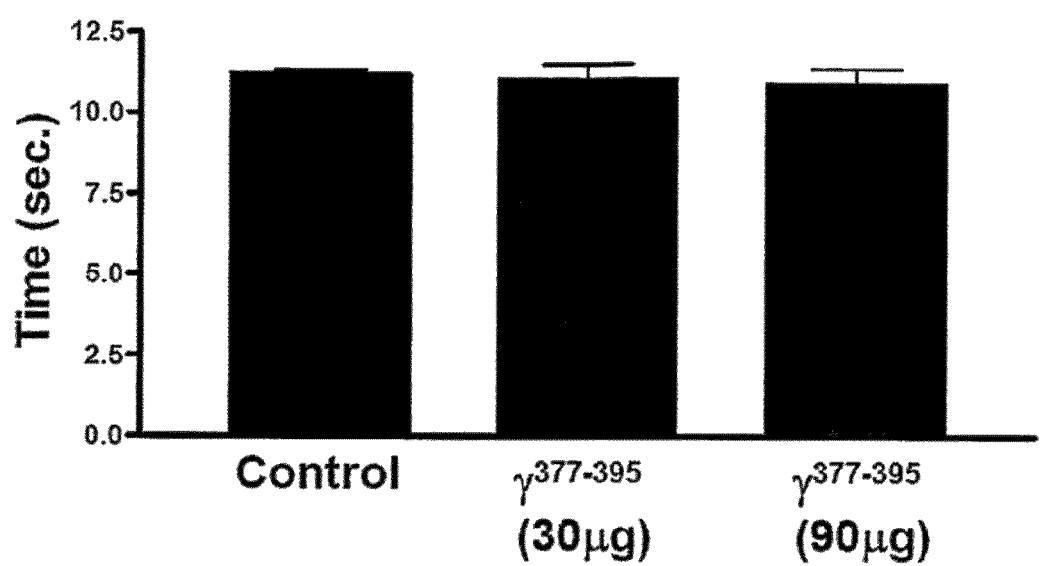

FIG. 29 depicts prothrombin times assayed in the presence of 30 of $\gamma^{377-395}$ peptide, the dose administered in vivo daily, and 90 µg of $\gamma^{377-395}$ peptide. Neither dose affected blood clotting times.

Figure 30:
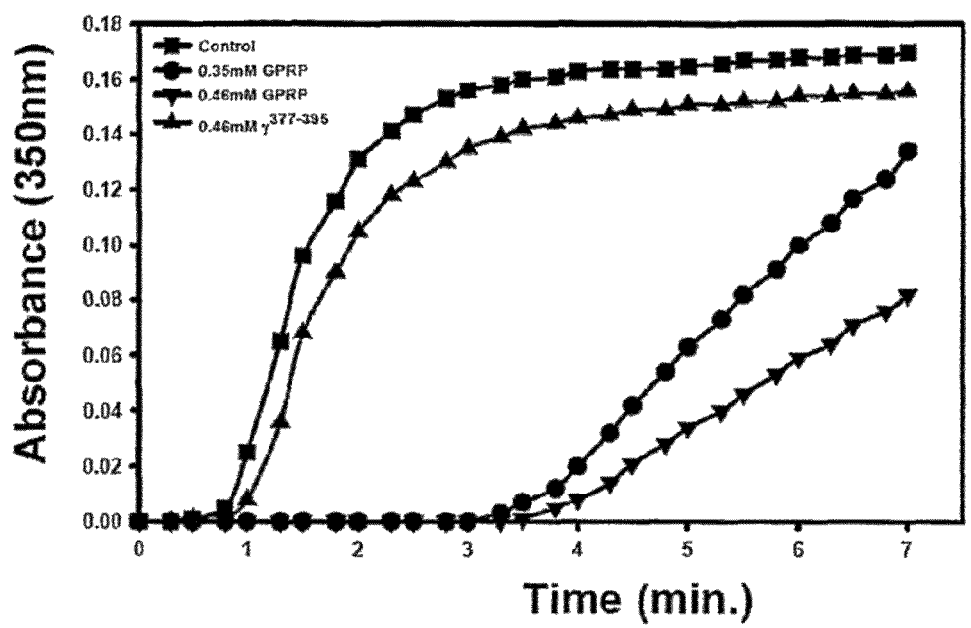

FIG. 30 depicts In vitro fibrin polymerization examined in the presence of the $\gamma^{377-395}$ peptide. GPRP, a known inhibitor of fibrin formation, significantly attenuated fibrin formation while the $\gamma^{377-395}$ peptide had no effect on fibrin polymerization.

Figure 31:
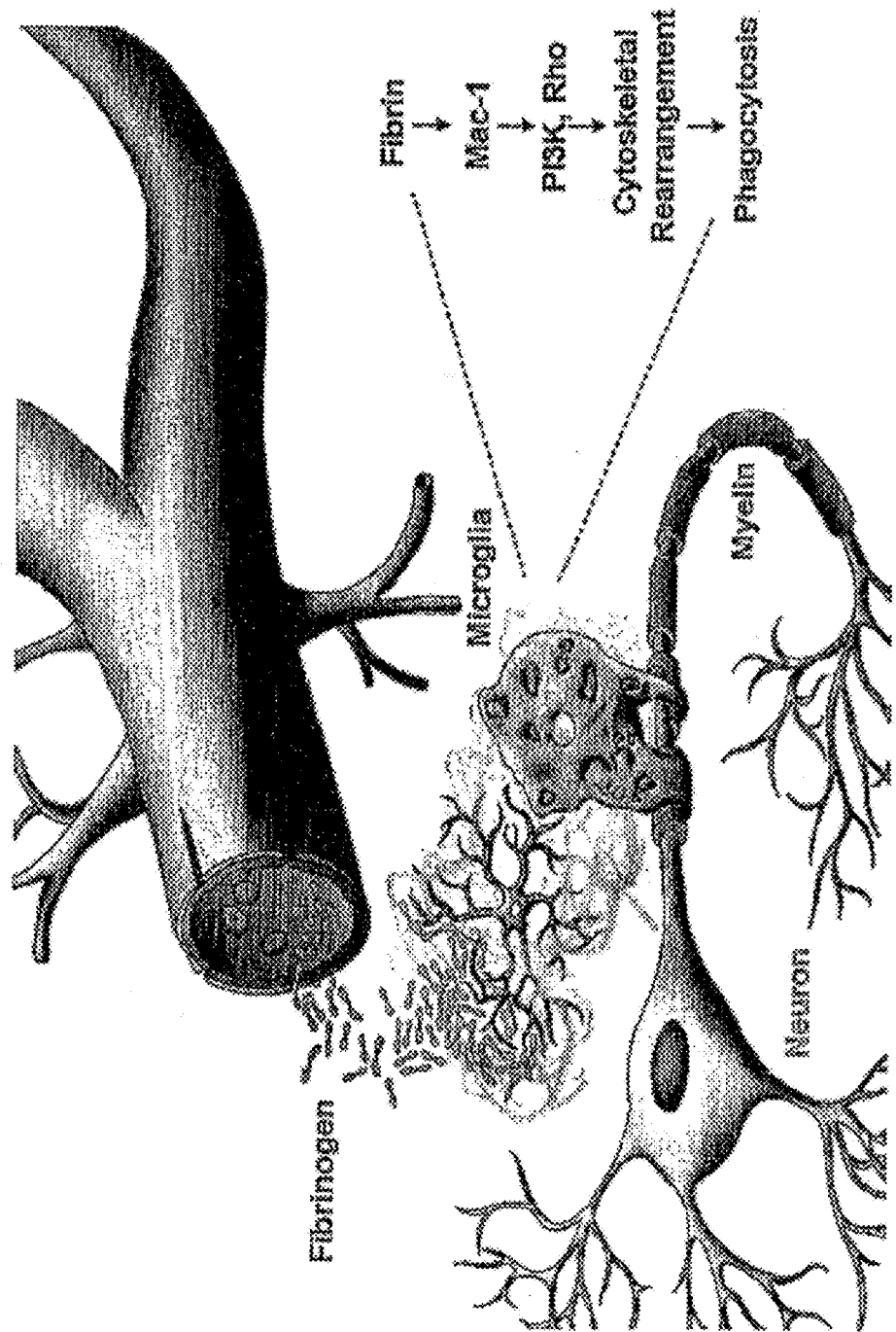

FIG. 31 illustrates a model for the role of fibrin-induced activation of microglia in inflammatory demyelination. BBB disruption permits the leakage of fibrinogen, the high affinity ligand for Mac-1, in the CNS parenchyma. Fibrinogen is converted to fibrin and functions as the spatial signal to induce local activation of microglia via activation of the Mac-1 integrin receptor and induction of signaling pathways downstream of Mac-1, such as Akt and Rho resulting in phagocytosis that could determine the extent of tissue damage in inflammatory demyelination.

Figure 32:
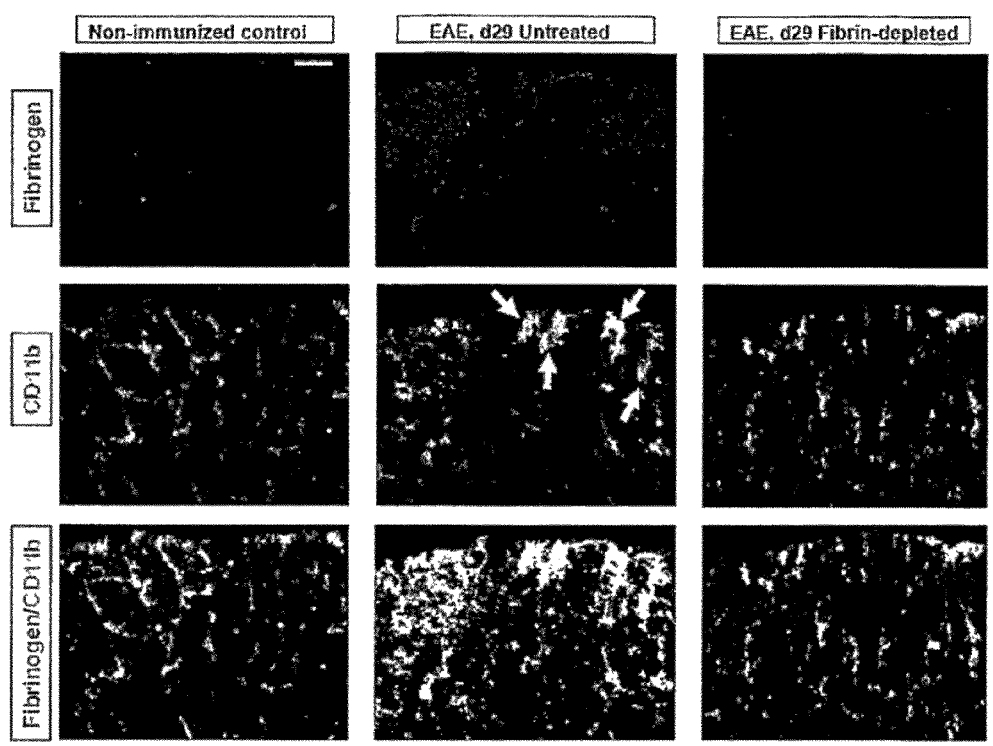

FIG. 32 depicts fibrin depletion decreasing in microglia activation in EAE. Spinal cord sections from mice immunized with $PLP_{139-151}$ peptide show increased CD11b-positive reactivity and fibrin deposits (middle column) as compared to non-immunized controls (left column) or fibrin-depleted mice (right column). Scale bar, 39 µm.

Figure 33:
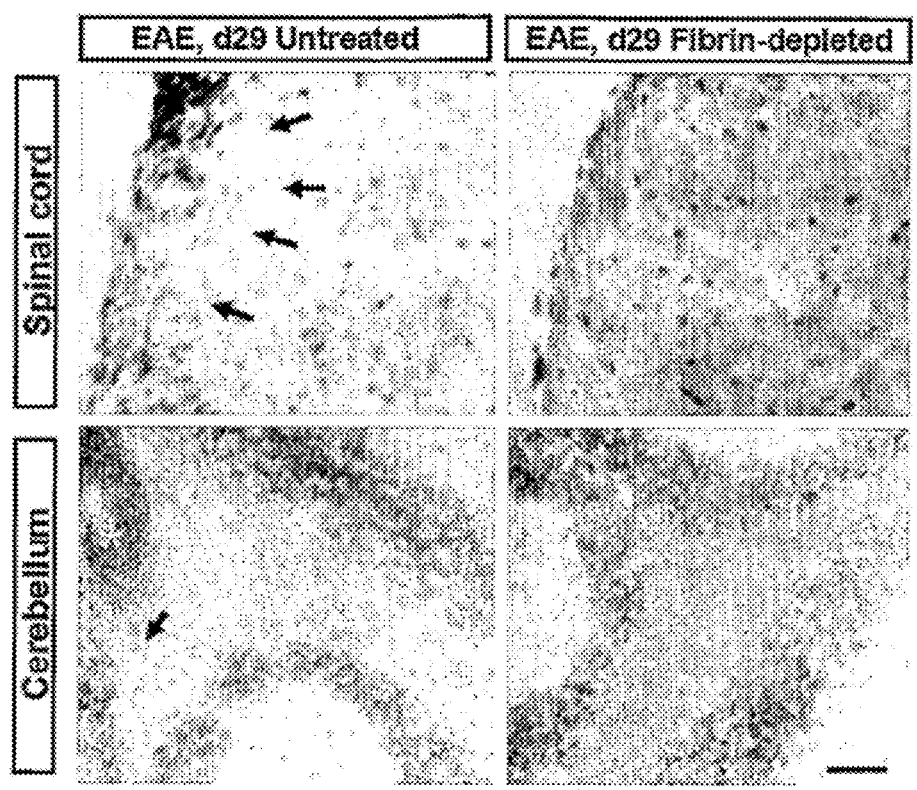

FIG. 33 depicts fibrin depletion reducing demyelinating lesions in EAE. Luxol Fast Blue/Nuclear Red staining of control cerebellum shows inflammation (asterisk) and demyelination (white area, arrow). Fibrin-depleted mice show normal cerebellar morphology. Staining of control spinal cord sections show large areas of demyelination (arrows) while fibrin-depleted spinal cord sections show normal myelin morphology. Scale bar, 42 µm (spinal cord), 105 µM (cerebellum).

Figure 34:
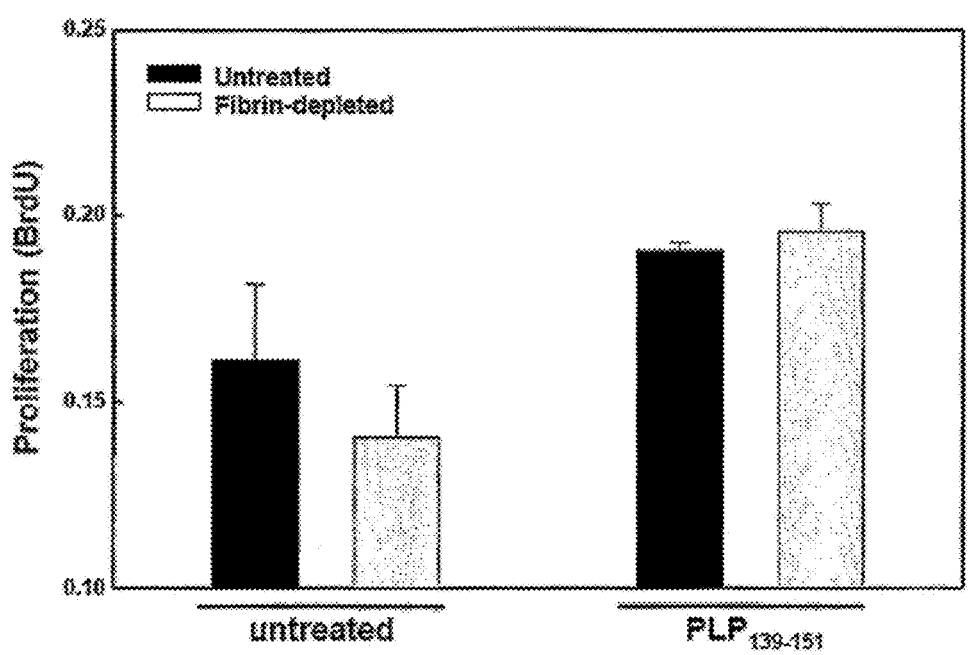

FIG. 34 depicts a splenocyte proliferation assay. Splenocytes from control and fibrin depleted mice subjected to $PLP_{139-151}$ EAE revealed no difference in proliferation under untreated or antigen stimulated conditions ($PLP_{139-151}$).

Figure 35:
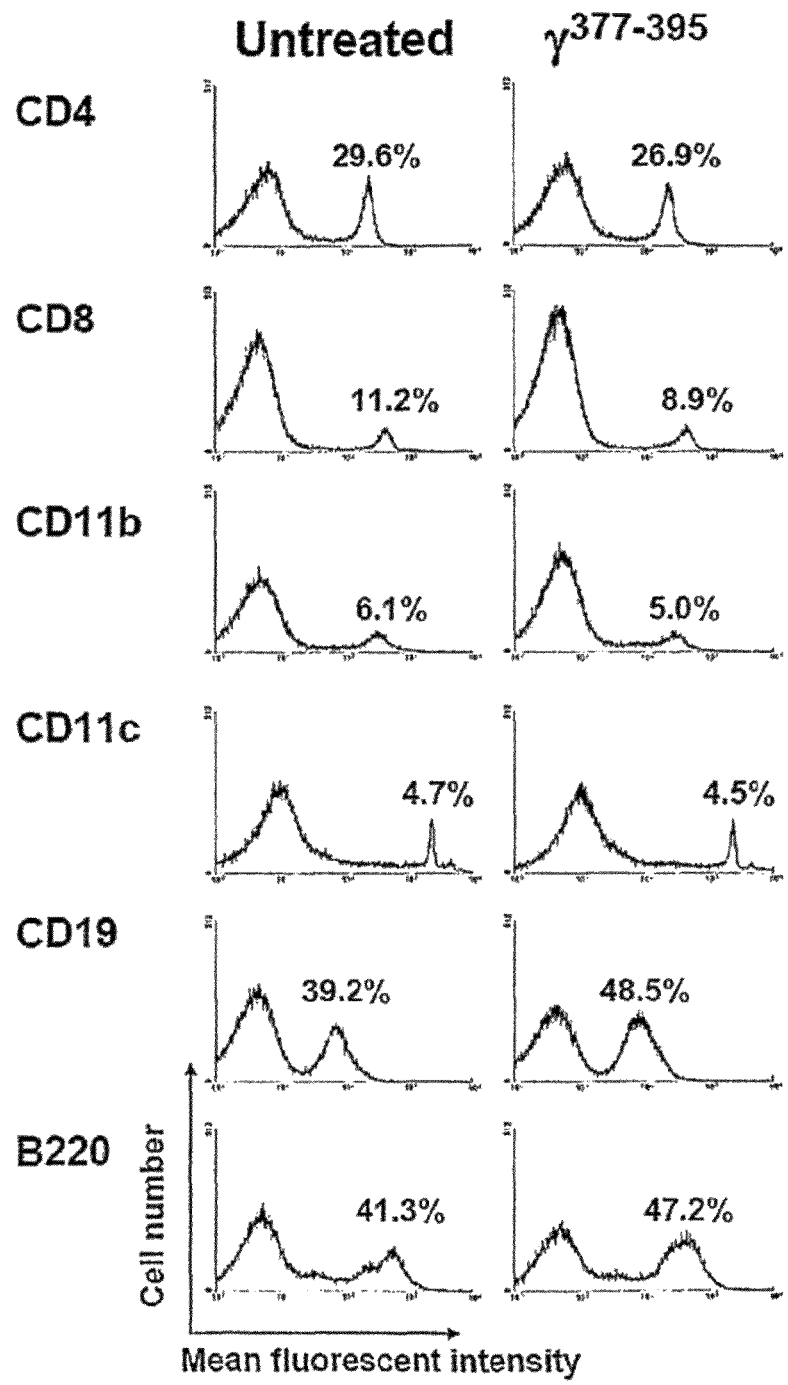
Figure 35A:
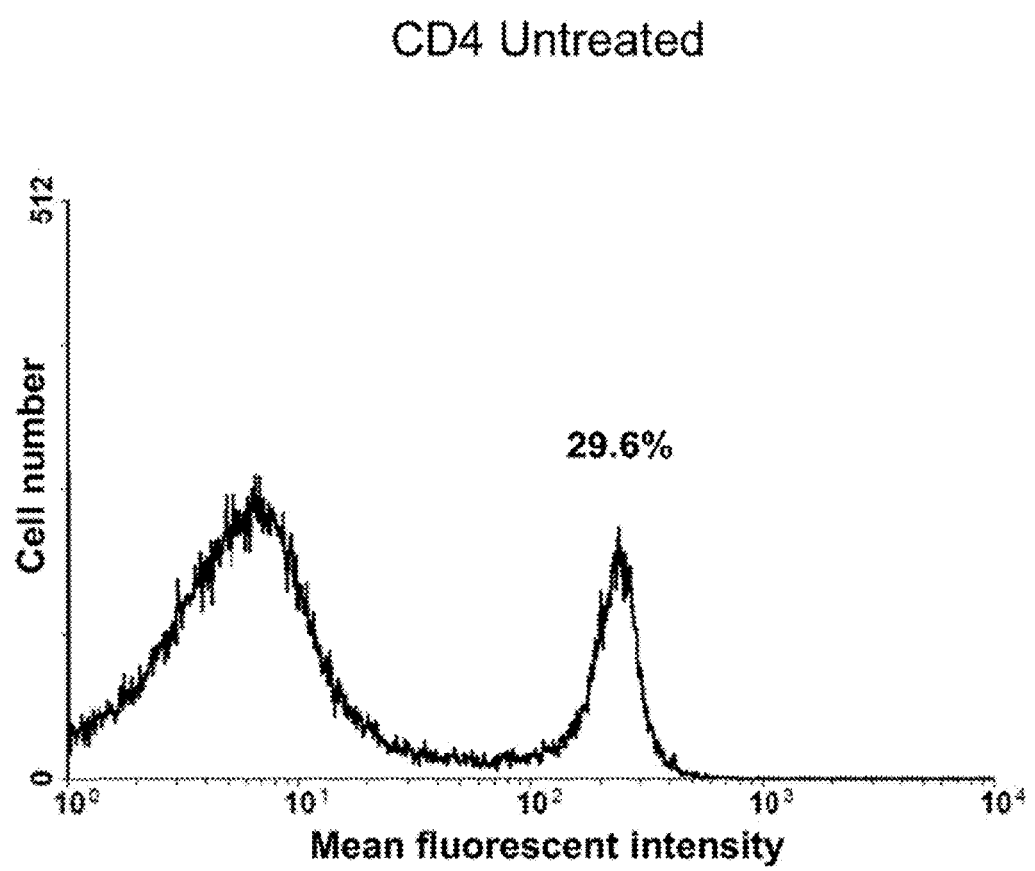
Figure 35B:
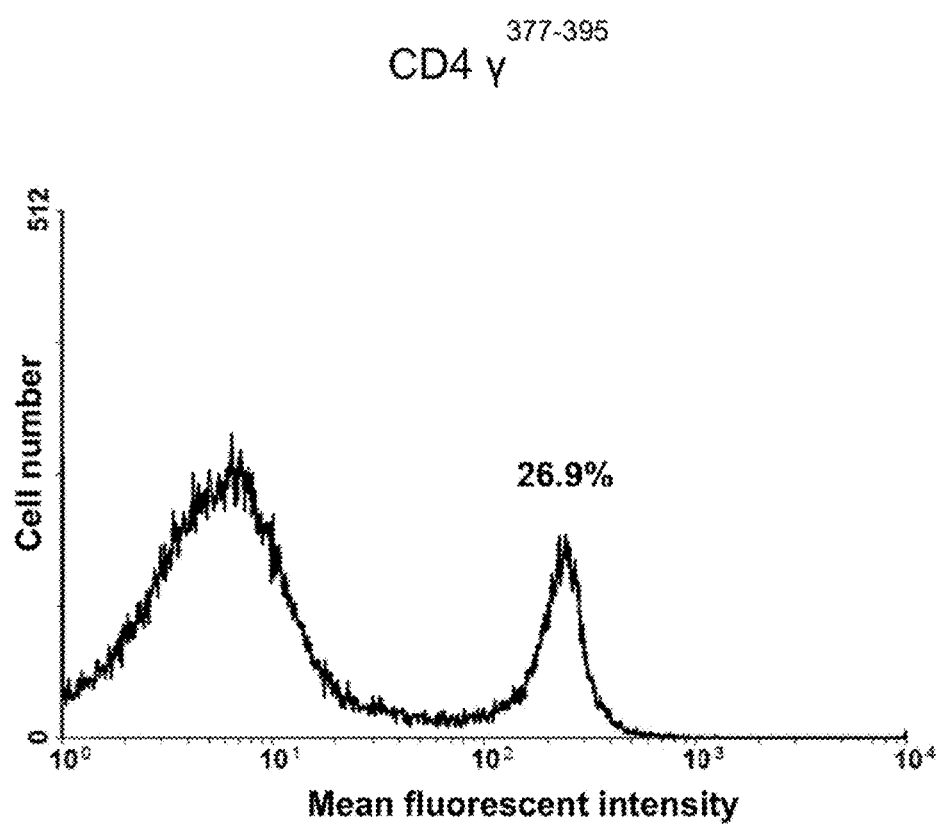
Figure 35C:
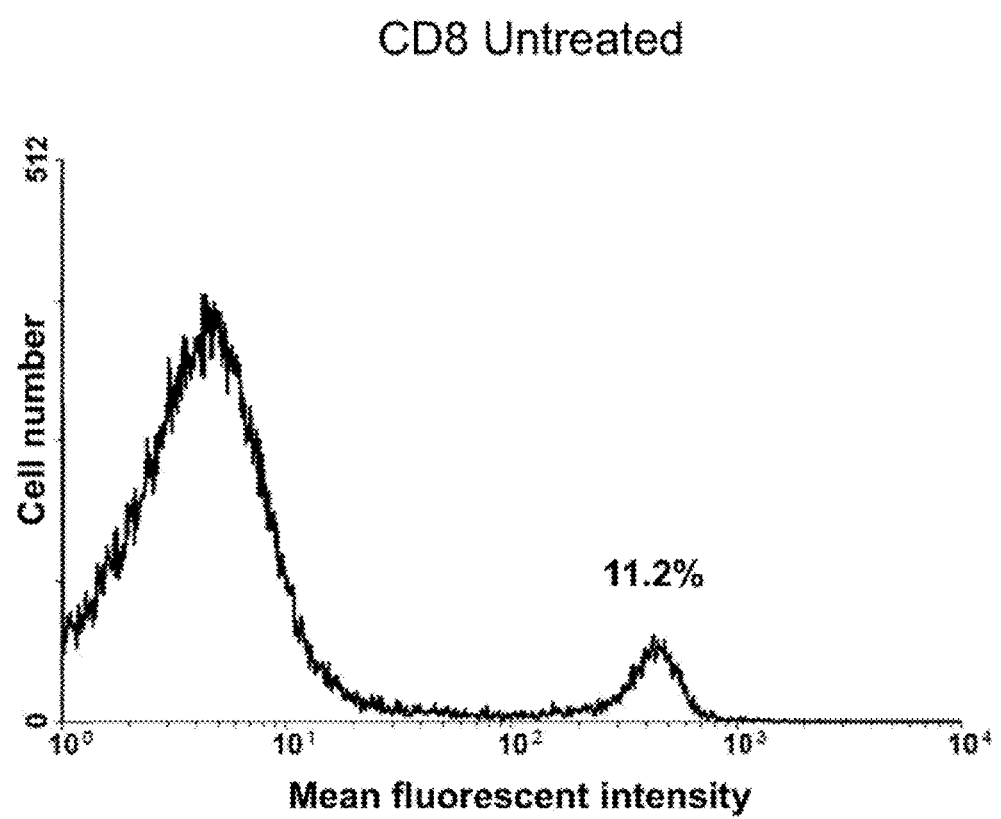
Figure 35D:
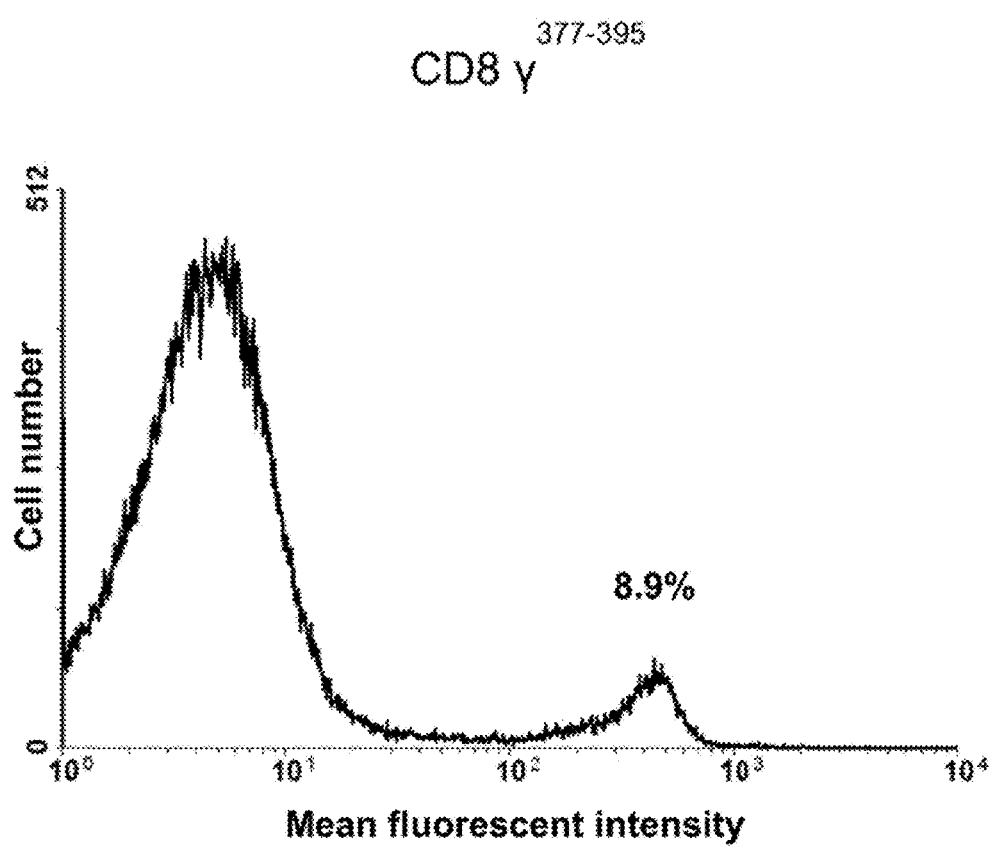
Figure 35E:
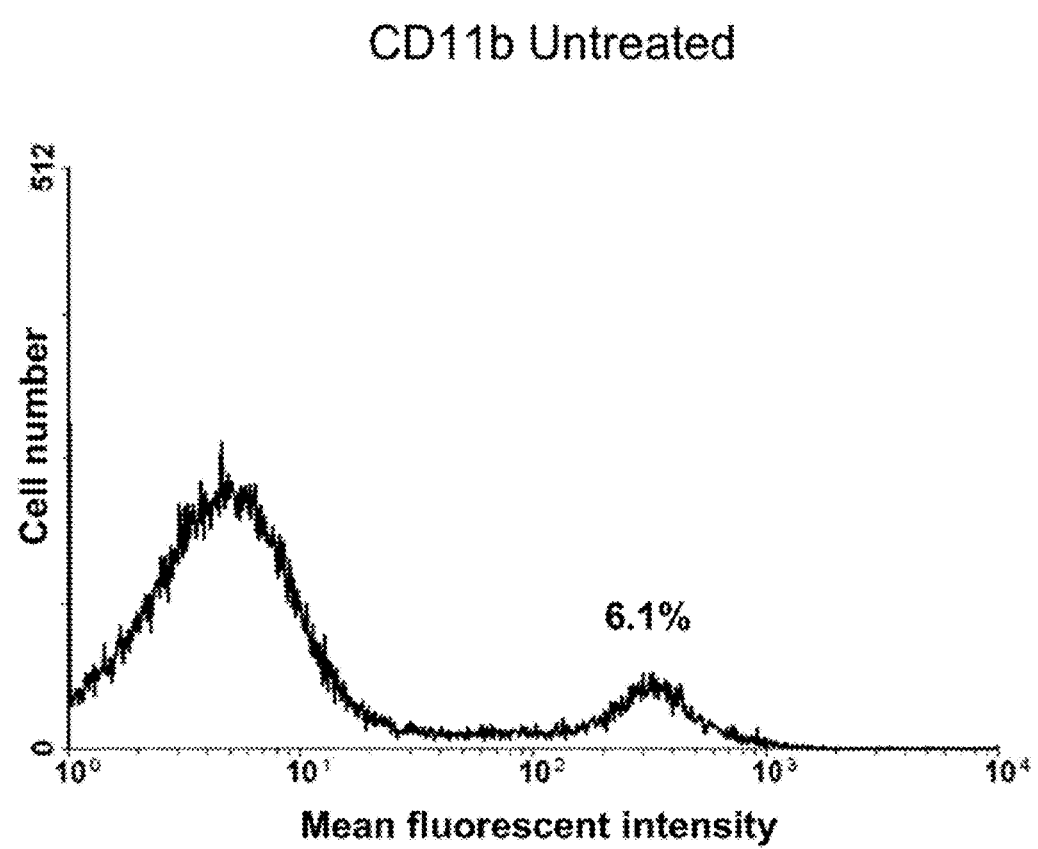
Figure 35F:
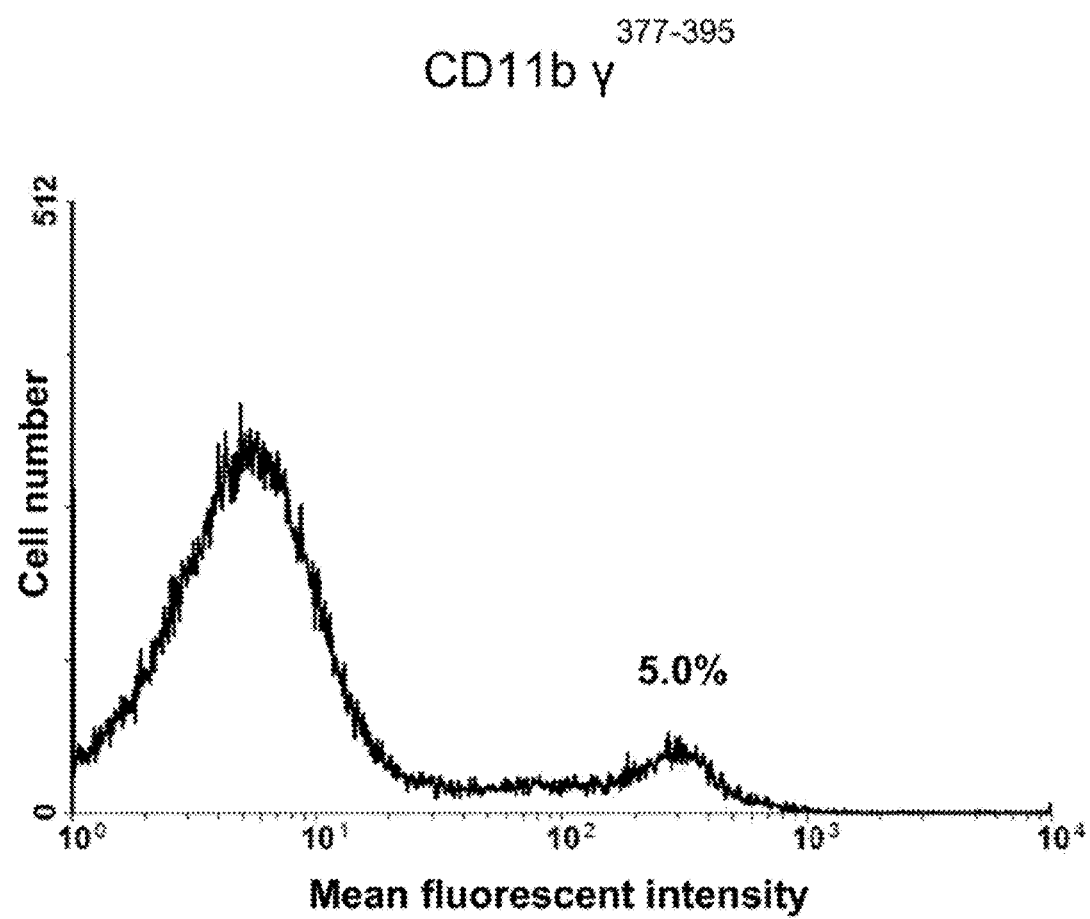
Figure 35G:
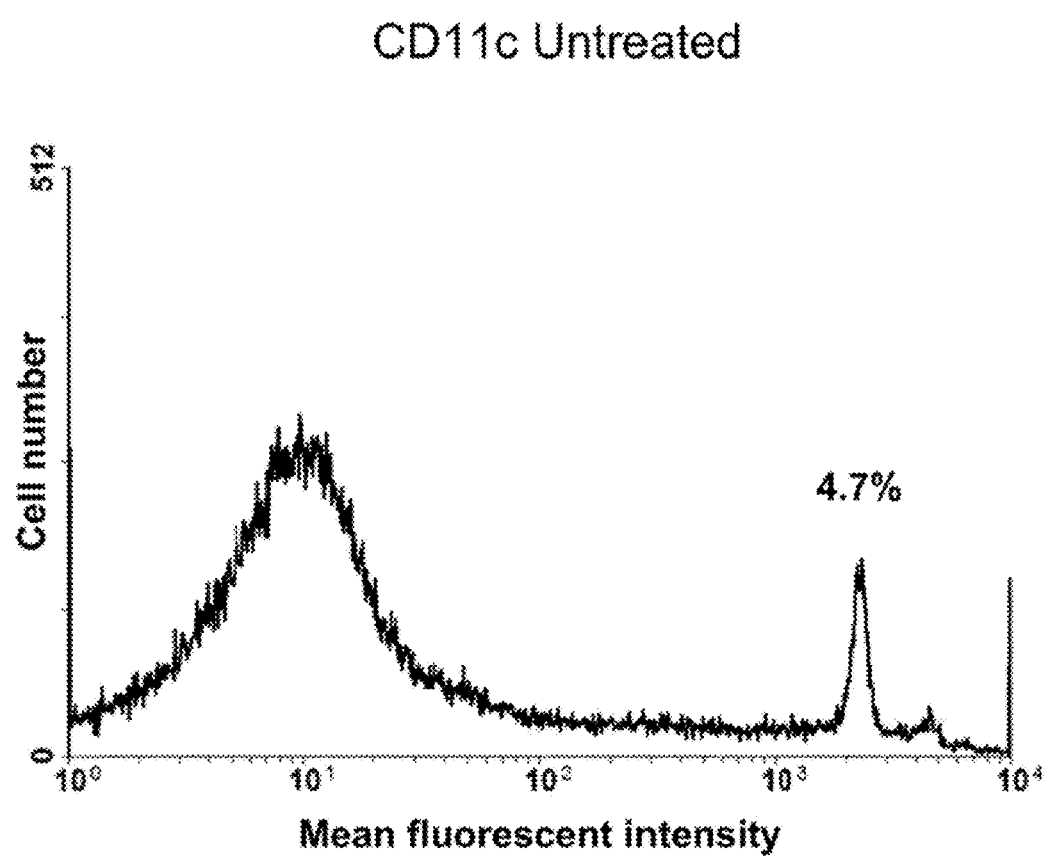
Figure 35H:
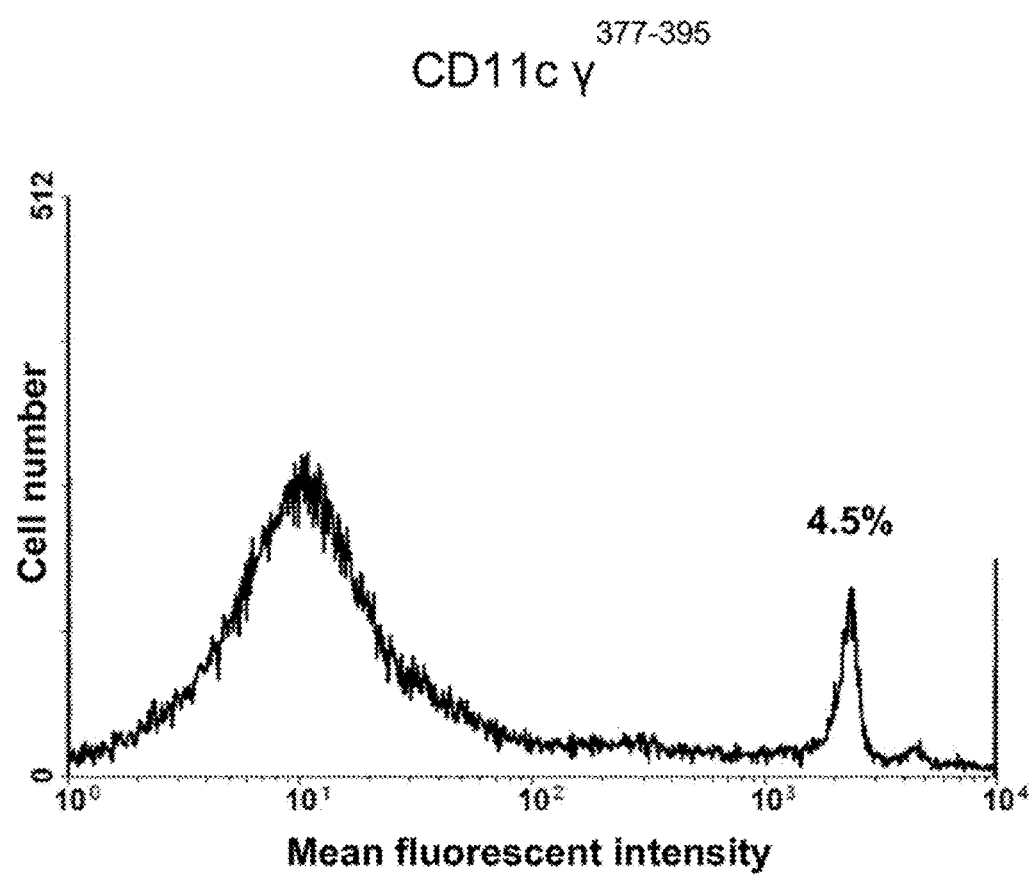
Figure 35I:
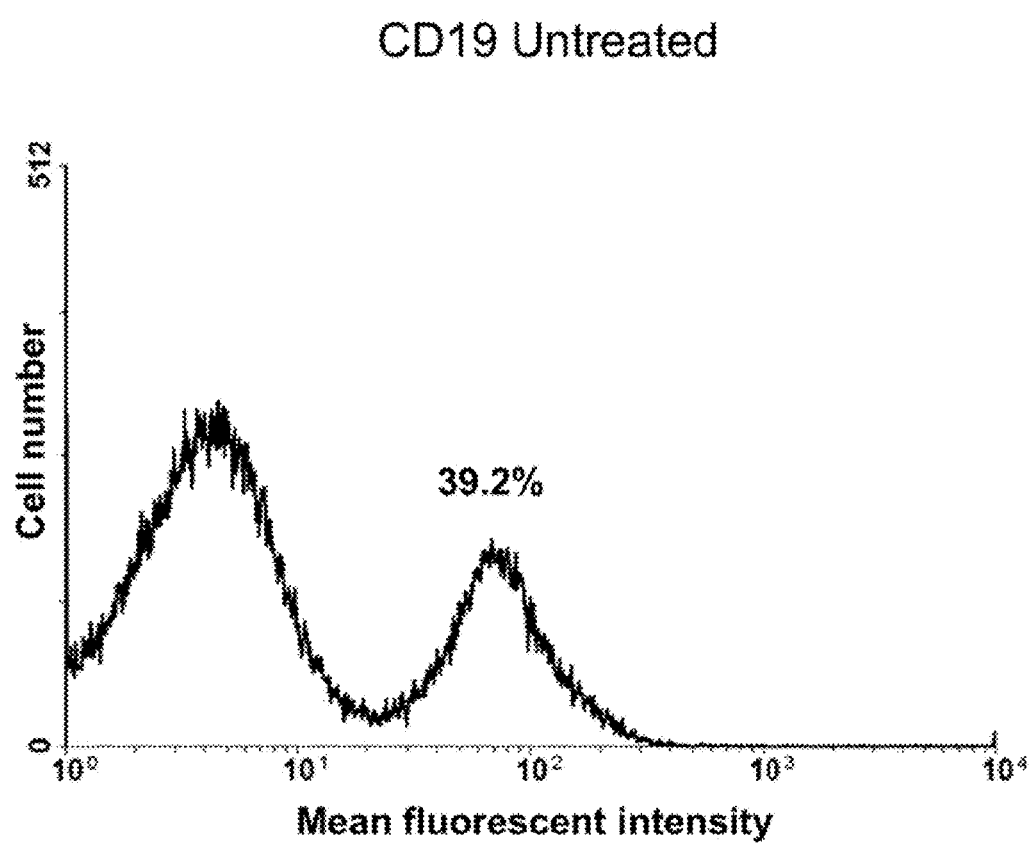
Figure 35J:
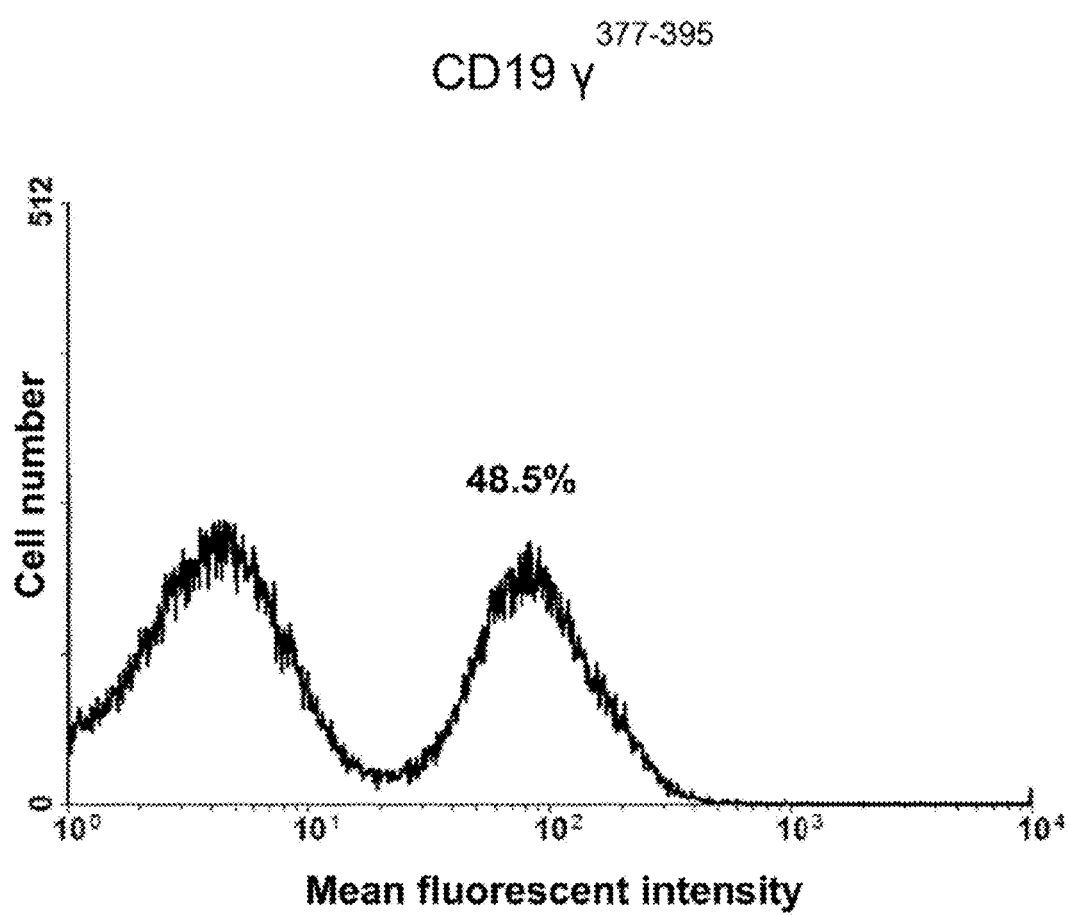
Figure 35K:
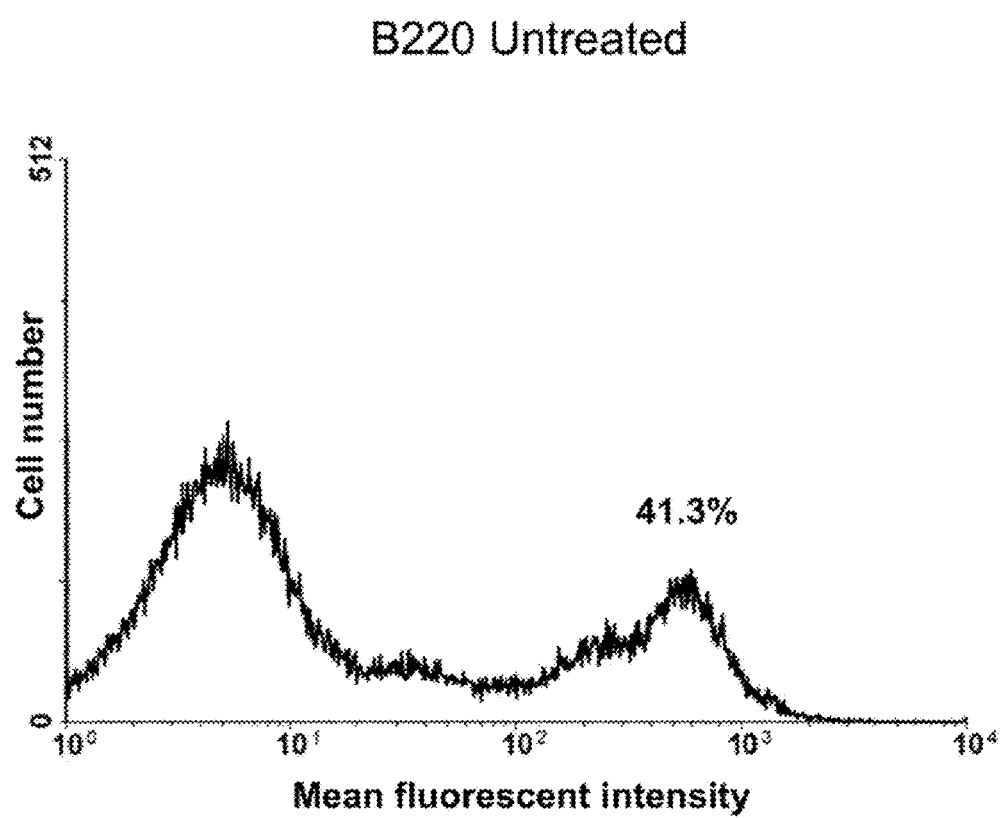
Figure 35L:
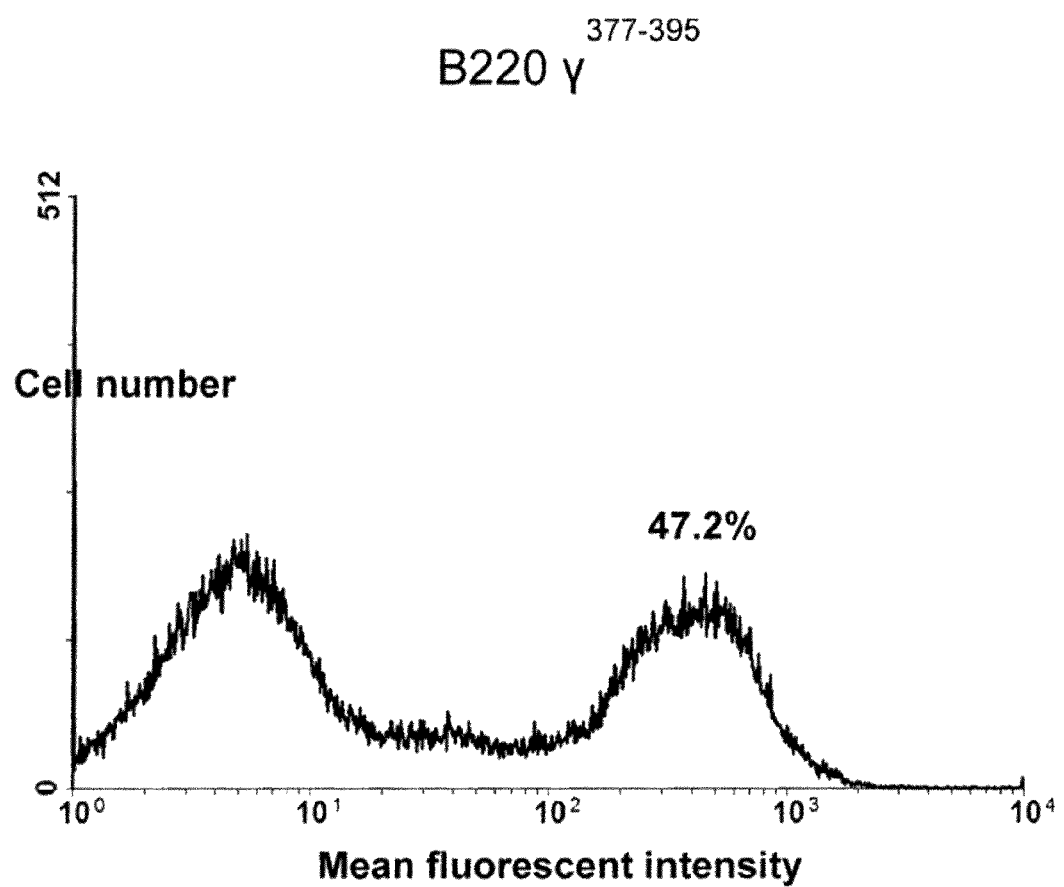

FIG. 35 depicts flow cytometry analysis on splenocytes from control or $\gamma^{377-395}$ peptide treated mice. Splenocytes were harvested from mice immunized with $PLP_{139-151}$ at the peak of the first relapse and immunostained with six markers of the peripheral immune response. The $\gamma^{377-395}$ peptide treatment had no significant effect on peripheral immune cells compared to control. (A) Untreated CD4 T cells; (B) $\gamma^{377-395}$ treated CD4 T cells; (C) Untreated CD8 T cells; (D) $\gamma^{377-395}$ treated CD8 T cells; (E) Untreated CD11b macrophages; (F) $\gamma^{377-395}$ treated CD11b macrophages; (G) Untreated CD11c dendritic cells; (H) $\gamma^{377-395}$ treated CD11c dendritic cells; (I) Untreated CD19 B cells; (J) $\gamma^{377-395}$ treated CD19 B cells; (K) Untreated B220 B cells; and (L) $\gamma^{377-395}$ treated B220 B cells.

DETAILED DESCRIPTION

The methods and compositions described herein utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. Pharmaceutical methods and compositions described herein, including methods for determination of therapeutically effective amounts, and terminology used to describe such methods and compositions, are well known to skilled artisans and can be adapted from standard references such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill 1996; and Rowe, R. C., et al., Handbook of Pharmaceutical Excipients, Fourth Edition, Pharmaceutical Press, 2003.

As used herein, the term "peptide" includes polypeptides consisting of, or consisting essentially of, a polypeptide chain of at least 10 amino acids up to about 30 amino acids, and salts thereof. A peptide can comprise a modified backbone and individual residue analogs.

The present inventors have found that the fibrin gamma 377-395 ($\gamma^{377-395}$) peptide, tyr-ser-met-lys-lys-thr-thr-met-lys-ile-ile-pro-phe-asn-arg-leu-thr-ile-gly (YSMKKTT-MKIIPFNRLTIG) (SEQ ID NO: 1) can block microglia activation in vitro, and is also able to reverse relapsing paralysis in an animal model of MS. This is the first demonstration of a therapy to reduce microglia activation. This treatment can lead to great improvements in patient health and quality of life, not only for MS therapy, but also for other neurodegenerative diseases with blood-brain barrier disruption or vascular injury such as spinal cord injury, stroke and Alzheimer's Disease.

Multiple Sclerosis (MS) is a chronic inflammatory demyelinating disease of the nervous system in which an inflammatory process is associated with destruction of myelin sheaths and later with axonal damage leading to permanent functional deficits, such as paralysis, and loss of vision (1). Resident microglia are considered responsible for the effector mechanism leading to demyelination via their ability to phagocytose myelin and secrete proinflammatory cytokines (2). Microglia are necessary not only for the maintenance, but also for the onset of inflammatory demyelination in central nervous system (CNS) autoimmune disease (3). The mechanisms of perivascular microglia activation in inflammatory demyelination as well as a strategy to limit their activation in MS has not been identified. This invention is not limited to MS, and teaches more broadly a method of treating nervous system disorders. MS is but one example of the diseases and conditions that can be treated using the novel compositions and methods taught herein. One skilled in the art can use this disclosure to treat the broad class of nervous system disorders. These include, but are not limited to, multiple sclerosis, spinal cord injury, stroke and Alzheimer's Disease.

The present inventor shows that inhibition of the inflammatory but not the coagulative properties of fibrinogen is sufficient to suppress clinical symptoms and disease pathogenesis in an animal model of MS. The inventor further shows that fibrinogen/Mac-1 interaction induces signal transduction pathways to activate microglia and has identified the $\gamma^{377-395}$ fibrin epitope (36) as a therapeutic target for MS. The results identify fibrinogen as a microglial activation signal. Without being limited by theory, the study suggests the following model for the role of fibrin in inflammatory demyelination (FIG. 31). 1) BBB disruption, which precedes lesion development and clinical symptoms in MS (6 45), permits the leakage of fibrinogen perivascularly in the brain. 2) Fibrinogen is converted to fibrin either by pro-coagulant factors produced in the nervous system or by factors from the blood that enter the brain together with fibrinogen. 3) Fibrinogen conversion to fibrin allows the exposure of the cryptic fibrinogen epitope $\gamma^{377-395}$ thus allowing interactions of fibrinogen with its Mac-1 integrin receptor. 4) Fibrin/Mac-1 interactions induce local activation of microglia. 5) Fibrin induces activation of Akt and Rho signaling in microglia resulting in cytoskeletal rearrangement leading to increased phagocytic capacity. 6) Fibrin-mediated microglia phagocytosis could determine the extent of tissue damage in MS. Given the colocalization of inflammatory demyelinating lesions in MS with fibrin deposition, the data suggest that fibrin/Mac-1 in the CNS parenchyma provides a spatial signal for microglia activation and determines the area of demyelination in MS. The inventor thus sought to design a therapeutic strategy that would block the damaging effects of fibrin in the nervous system without affecting its beneficial effects in blood coagulation by identifying and targeting the fibrin receptor in the nervous system, and determined that the $\gamma^{377-395}$ peptide of fibrin induces a reduction of iNOS-positive microglia, suggesting that inhibition of fibrin/Mac-1 interaction reduces microglia activation that in MS could mediate secondary damaging effects on other cell types of the nervous system.

We sought to design a therapeutic strategy that would block the damaging effects of fibrin in the nervous system without affecting its beneficial effects in blood coagulation by identifying and targeting the fibrin receptor in the nervous system. Interaction of fibrin with its receptors has been previously used for drug development. Fibrin mediates blood coagulation via binding to the platelet integrin receptor $\alpha_{11b}\beta_3$. Development of an antibody that blocks binding of fibrin to its $\alpha_{11b}\beta_3$ receptor (RcoPro®, abciximab) is a successful thrombolytic treatment for atherosclerosis (20). The $\alpha_{11b}\beta_3$ integrin receptor is expressed exclusively by platelets and not by cells in the nervous system. We hypothesized that if we identified the specific cell type in the nervous system that is affected by fibrin and the receptor that fibrin utilizes to mediate this effect; we would be able to inhibit the cellular functions of fibrin in the nervous system without affecting its coagulative properties in the blood.

Recent evidence showed that paralysis of CD11b-positive microglia ameliorates inflammatory demyelination in the presence of peripheral T-cells and macrophages (3). Myelin phagocytosis is thought to be subjected to modulation between inactive and active states of the Mac-1 receptor (23). Immobilized fibrinogen, insoluble fibrin but not soluble fibrinogen have been identified as physiological, high-affinity ligands for Mac-1 (15, 24, 25). Interestingly, in MS lesions fibrin deposition colocalizes with areas of activated microglia (11). Here we show that fibrin serves as an environmental signal to induce the differentiation of microglia to phagocytes via the Mac-1 (CD11b/CD18) integrin receptor. Moreover, the fibrin $\gamma^{377-395}$ peptide (the binding epitope of fibrin to CD11b) functions as an inhibitor of microglia activation. Finally, we use multiple approaches, such as knock-in mice, vaccination and intranasal peptide delivery to test the efficacy of targeting the fibrin $\gamma^{377-395}$ epitope as a novel therapeutic strategy for inflammatory demyelination. Our study shows for the first time that fibrin induces microglia activation and that targeting the inflammatory, but not the coagulative properties of fibrinogen is sufficient to suppress microglia activation and inflammatory demyelinating disease.

In this study we show for the first time that inhibition of the inflammatory but not the coagulative properties of fibrinogen is sufficient to suppress clinical symptoms and disease pathogenesis in an animal model of MS. We show that fibrinogen/Mac-1 interaction induces signal transduction pathways to activate microglia and have identified the $\gamma^{377-395}$ fibrin epitope as a therapeutic target for MS. Our results identify fibrinogen as a microglial activation signal. Fibrinogen is not present in the healthy CNS, but only leaks in the brain after BBB disruption, thus serving as an environmental "danger" signal (4). Moreover, fibrinogen contains a binding motif for Mac-1 that allows the induction of ligand/receptor mediated activation of microglia.

The present study identifies fibrinogen as a ligand for Mac-1 on microglia cells. Complement and in particular iC3b is well established as a ligand for Mac-1 (28). The presence of immunoglobulins and activated complement is restricted to the pattern II MS lesions (1). Since microglia activation and phagocytosis is a common feature for all subtypes of MS, other factors in the demyelinating lesion could potentially mediate microglia activation. Since BBB disruption is a common feature for different types of MS lesions, our study suggests that fibrin could serve as a broad activation signal for microglia in the CNS. The $\gamma^{377-395}$ peptide induced a reduction of iNOS-positive microglia, suggesting that inhibition of fibrin/Mac-1 interaction reduces microglia activation that in MS could mediate secondary damaging effects on other cell types of the nervous system, such as neuronal death.

The identification of Mac-1 integrin as the fibrin receptor that mediates microglia activation was the basis to specifically block the functions of fibrin in the nervous system without affecting its physiological functions in blood coagulation. Two previous studies have determined that inhibiting the coagulative properties of fibrinogen by use of anti-coagulants such as ancrod in a prophylactic manner can ameliorate symptoms of EAE (19, 47). In the present study the inventor further demonstrates that administration of ancrod after the onset of paralysis can suppress EAE (FIGS. 11-13 and FIGS. 32-33). However, the use of anti-coagulants could have limited clinical applications to a chronic disease such as MS due to adverse hemorrhagic effects caused by prolonged anti-coagulant treatment. Since $\alpha_{11b}\beta_3$ binds fibrinogen at the $\gamma^{408-411}$ epitope, targeting the Mac-1 binding epitope of fibrinogen either genetically (15), or pharmacologically (our study) does not affect the coagulation properties of fibrinogen. Moreover, the $\gamma^{377-395}$ is a cryptic epitope in the fibrinogen molecule and is exposed only when fibrinogen is immobilized or converted to fibrin (25, 36). The present investigations demonstrate that inhibition of the interaction of fibrin with Mac-1 either genetically or pharmacologically inhibits microglia activation and can suppresses paralysis in mice.

Fibrin/Mac-1 mediated activation of monocytes cells is well established (17). Our study shows that fibrinogen depletion or treatment with the $\gamma^{377-395}$ peptide attenuates the clinical symptoms in EAE by primarily ameliorating the microglia/macrophage response without interfering with T cell activation. These results are in accordance with previous studies that have established that depletion of macrophages (43) or microglia (3) in EAE results in amelioration of clinical symptoms in the presence of functional T cell activation. In addition to CD11b, fibrinogen binds to the CD11c chain of the CD11c/CD18 integrin (48). The $\gamma^{377-395}$ fibrin peptide blocks the binding of fibrinogen to both CD11b and CD11c integrins (36). The CD11c-positive perivascular dendritic cells are responsible for the presentation of myelin antigens (49, 50).

To investigate how fibrinogen increased microglia phagocytosis, we examined whether fibrinogen regulates RhoA and PI3K, the two major signaling pathways that mediate the cytoskeletal rearrangements for the induction of phagocytosis (23). We first examined if fibrinogen induced RhoA activation in microglia, since RhoA is required for type II, Mac-1-mediated phagocytosis (24). Fibrinogen induced a 1.9-fold increase of active RhoA as assessed by an increased interaction with GST-Rhotekin binding protein which binds only GTP-bound, or active, RhoA (FIG. 9). In comparison, LPS stimulation resulted in a 2.4-fold activation of Rho. We next examined whether fibrinogen stimulation activated PI3K, since phosphatidylinositol 3,4,5-trisphosphate (PIP3) is required for the progression of Mac-1 phagocytosis (25). Production of the signaling lipid, PIP3, was assessed by examining a direct downstream effector, the serine/threonine kinase Akt. Fibrinogen stimulation resulted in a 24-fold increase in Akt phosphorylation while LPS stimulation resulted in a 34-fold increase (FIG. 9). Furthermore, blocking the PI3K signaling pathway using LY294002, inhibited the fibrin-induced increase of phagocytosis in microglia (FIG. 8), suggesting that PI3K is downstream of fibrin/Mac-1 signaling in microglia cells. Overall, these data demonstrate that fibrinogen activates both RhoA and Akt, two major pathways in microglia that redistribution of the cytoskeleton, and ultimately resulting in increased phagocytosis.

Our in vitro data show that fibrin activates microglia cells. To investigate whether fibrin is required for the activation of Mac-1 positive cells in vivo, we examined whether fibrin depletion would reduce the activation of CD11b-positive cells in Experimental Autoimmune Encephalomyelitis (EAE). We administered the anti-coagulant ancrod (26) in an established remitting-relapsing model of EAE induced by the $PLP_{139-151}$ peptide in SJL/J mice (27) after the development of the first paralytic incidence. Untreated mice show dramatic activation of CD11b+ cells characterized by thick processes (FIG. 11, left panel, green) 29 days after immunization. By contrast, in mice treated with ancrod CD11b+ cells appear with ramified morphology (FIG. 11, right panel, green) resembling CD11b+ cells that are present in the normal spinal cord of non-immunized mice (FIGS. 23-27). Similar to MS lesions (9), areas of colocalization of fibrin. (red) with IsoB4 positive cells (green) are observed in untreated mice (data not shown). Histopathology was performed on cerebellum and spinal cords from mice treated with ancrod as well as controls. LFB/NR staining revealed extensive inflammatory lesions in the cerebellum (FIGS. 28-30, asterisk) and the spinal cords of untreated mice. By contrast, mice treated with ancrod did not show signs of inflammation (FIGS. 28-30).

Demyelination was observed in the cerebellum and spinal cord (FIGS. 28-30, arrows) of untreated mice, while demyelination was minimal in ancrod-treated mice. Quantification in the cerebellum and spinal cord showed a 7-fold and a 2-fold decrease of the demyelinated area in ancrod-treated versus untreated control mice. Immunostaining for T cells using an anti-CD3 cell marker, did not reveal differences in the number of T cells between ancrod-treated and untreated mice (data not shown). In addition, there was no difference in proliferation upon stimulation with $PLP_{139-151}$ in spleenocytes isolated from untreated and ancrod-treated mice, further suggesting that CD11b+ cells are the major cell target of fibrin in the nervous system. Fibrin-depleted mice recovered faster from the first paralytic incidence and in contrast to control mice never relapsed (FIG. 12). In a rotarod behavioral test, performed before the second relapse of the untreated group, fibrin-depleted mice showed a 3-fold increase of motor strength and coordination when compared to the untreated group (FIG. 13). Overall, these results suggest that fibrin is a major contributor to the local activation of CD11b+ cells in vivo. In addition, this is the first demonstration that anti-coagulants improve clinical symptoms and reduce inflammatory demyelination when administered after the onset of paralytic symptoms.

To examine the contribution of fibrinogen signaling through Mac-1 in inflammatory demyelination in vivo, we subjected mice with a knock-in mutation at the C-terminus of the gamma chain of fibrinogen to MOG-induced EAE (28). This mutation of seven amino acids at residues ($N^{390}RLSIGE^{396}$) (SEQ ID NO: 3) to alanine residues ($A^{390}AAAAAA^{396}$) (SEQ ID NO: 4) abolishes fibrinogen binding to the Mac-1 receptor. These mice, termed $Fib^{Mac-1}$, and their age- and sex-matched littermate controls ($Fib^{wt}$) were immunized with MOG peptide (FIG. 14). $Fib^{Mac-1}$ mice showed an average clinical score of 2.2 (ataxia) at day 17 after immunization, while the $Fib^{wt}$ mice developed clinical symptoms of paralysis, showing an average score of 3.66 (hind limb paralysis). In the $Fib^{wt}$ mouse group 11 out of 15 mice were paralyzed, by contrast to 4 out of 16 of the $Fib^{Mac-1}$ mice (clinical score>3) (FIG. 15), further demonstrating decreased severity of EAE. In addition to the clinical score, motor function was tested by rotarod analysis. $Fib^{Mac-1}$ mice showed a 1.5 fold increase in motor skills, when compared to $Fib^{wt}$ mice ($Fib^{Mac-1}$, 269±9 sec vs. $Fib^{wt}$, 169±23 sec, P<0.05) (FIG. 18). Analysis of the inflammatory index showed a three fold decrease in $Fib^{Mac-1}$ mice, when compared to $Fib^{wt}$ (FIG. 16). In accordance, histological analysis of spinal cord sections revealed a decrease in the extent of IsoB4-positive cells in $Fib^{Mac-1}$ mice, when compared to $Fib^{wt}$ controls (FIG. 19). Decrease in clinical severity was also observed at later time points after the immunization (FIGS. 14 and 15). In the $Fib^{wt}$ mouse group, 4 out of 15 mice were in moribund state (clinical score 5), by contrast to 1 out of 17 of the $Fib^{Mac-1}$ mice (FIG. 17). Overall, these results suggest that the $\gamma^{390-396}$ binding site of fibrinogen to Mac-1 determines the severity of inflammatory demyelination.

Both the in vitro (FIGS. 5-10) and in vivo experiments (FIGS. 14-19) show that fibrinogen signaling through the Mac-1 receptor contributes to microglia activation and regulates the severity of inflammatory demyelination in EAE. Biochemical studies identified that the $\gamma^{377-395}$ peptide (YSMKKTTMKIIPFNRLTIG) (SEQ ID NO: 1) blocks fibrin binding to Mac-1 (29). The $\gamma^{377-395}$ is a cryptic epitope in the fibrinogen molecule and is exposed only when fibrinogen is immobilized or converted to fibrin (25, 36). We used 200 µM of peptide, a concentration shown to inhibit adhesion of Mac-1 overexpressing cells to immobilized fibrinogen (37), to examine whether the $\gamma^{377-395}$ peptide could inhibit microglia activation. Fibrinogen treatment resulted in 71±4.9% of activated microglia, when compared to 38.3±9.8% after addition of the $\gamma^{377-395}$ peptide (P<0.05) (FIGS. 20 and 21), suggesting that the $\gamma^{377-395}$ peptide reduced fibrin-mediated microglia activation. The $\gamma^{377-395}$ peptide did not affect the activation state of untreated microglia and did not inhibit LPS-mediated microglia activation (FIG. 21), further suggesting the specificity of $\gamma^{377-395}$ to block activation of Mac-1 by fibrin. In accordance, examination of Akt phosphorylation showed that the $\gamma^{377-395}$ peptide could specifically inhibit fibrin-mediated and not LPS-mediated phosphorylation of Akt (FIG. 22). Overall, these results indicated that inhibition of fibrin/Mac-1 interactions by the $\gamma^{377-395}$ peptide inhibits both the morphological activation and the signaling cascade induced by fibrin-mediated activation of the Mac-1 microglia receptor.

Since genetic studies showed that the $\gamma^{377-395}$ binding epitope of fibrinogen to Mac-1 is not involved in coagulation (15), but is sufficient to inhibit fibrin mediated microglia activation (FIGS. 14-22), we examined whether blocking exclusively the inflammatory properties of fibrinogen in vivo using the $\gamma^{377-395}$ would be sufficient to ameliorate Experimental Allergic Encephalitis (EAE). We therefore examined the effects of in vivo administration of the $\gamma^{377-395}$ fibrin peptide on microglia activation and clinical progression in an animal model for MS. We first assessed the effects of vaccination against $\gamma^{377-395}$ peptide. Vaccination with $\gamma^{377-395}$ peptide before the induction of EAE resulted in a significant reduction in disease penetrance and clinical symptoms. All control mice (15/15) developed clinical symptoms of EAE. By contrast, only 53% of the vaccinated mice (8/15) developed EAE. Moreover, mice vaccinated with the $\gamma^{377-395}$ peptide showed an average clinical score of 1.1, while the control group showed a score of 2.5 (FIG. 23, P<0.01). In a rotarod test, vaccinated mice showed a 76% increase in motor strength and coordination, when compared to the control mice. Quantificative histopathological analysis showed reduced pathology in the brain (index of 1.5±2 vs. 2.3±1) and spinal cord (index of 6.5±5.9 vs. 12±5.2) from $\gamma^{377-395}$ peptide vaccinated mice as compared to control mice.

Since vaccination is a preventive treatment, we further assessed whether $\gamma^{377-395}$ peptide would be beneficial if administered after the onset of disease. We administered intranasally (i.n.) 30 μg of $\gamma^{377-395}$ peptide daily after the first paralytic episode in remitting relapsing EAE (35). Intranasal delivery is a non-invasive delivery method, and results in a higher degree of drug delivery to the nervous system and in a lower degree of systemic drug delivery to tissues such as liver and lymph nodes, when compared to intravenous (i.v.) delivery (38). Intranasal delivery has been previously shown to be effective as a method of drug delivery in EAE (39-41). $\gamma^{377-395}$ peptide treated mice (n=14) in contrast to control mice (n=13) did not relapse (FIG. 24). Peptide treated mice showed a 1.4-fold increase of motor functions when compared to the control mice after the first relapse on day 29.

Immunohistochemical analysis using Mac-3, a microglia/macrophage marker, revealed reduction of activated cells in the peptide-treated (FIG. 26), as compared to control animals (FIG. 25). In addition, iNOS, a major product of activated CD11b-positive microglia in EAE (42), was reduced in the $\gamma^{377-395}$ peptide-treated animals (FIG. 26, inset). Quantification of the histopathological analysis shows reduction in both Mac-3 and iNOS, while there are no major differences in T cell infiltrates (FIG. 27). We further examined whether the $\gamma^{377-395}$ peptide affected the peripheral immune response. FACS analysis on splenocytes of mice immunized with PLP$_{139-151}$ using six markers for peripheral immune cells, namely CD4 and CD8 T cells, CD11b macrophages, CD11c dendritic cells, and CD19 and B220 B cells, did not reveal any differences between untreated and $\gamma^{377-395}$ peptide treated animals (FIG. 35), suggesting that similar to systemic fibrin depletion (FIG. 34) the $\gamma^{377-395}$ peptide does not affect the peripheral immune response. These results are in accordance with prior studies where depletion of macrophages (43) or microglia (3) resulted in dramatic reduction of clinical symptoms in EAE even in the presence of functional T cells.

Several studies have demonstrated both in vivo and in vitro that fibrinogen interacts with different cellular receptors via non overlapping epitopes (for review see (16)). Fibrinogen regulates blood coagulation by engaging the platelet $\alpha_{11b}\beta_3$ integrin receptor via its $\gamma^{408-411}$ epitope, while it mediates inflammatory processes by engaging the Mac-1 receptor via its $\gamma^{377-395}$ epitope. As a result fibrinogen knock-in mice, where the $\gamma^{390-396}$ Mac-1 binding site has been mutated show normal coagulation properties, such as platelet aggregation, thrombus formation and clotting time (15). To determine whether the $\gamma^{377-395}$ peptide interfered with blood coagulation, we examined its effects on the coagulative properties of fibrinogen both in vivo and in vitro. As expected, the $\gamma^{377-395}$ peptide did not affect coagulation in mice (FIG. 28) or prothrombin time (FIG. 29). Moreover, in an in vitro fibrin polymerization assay the $\gamma^{377-395}$ peptide did not alter the polymerization time of fibrin (FIG. 30). By contrast, the GPRP peptide, an established inhibitor of clot formation (44), inhibits fibrin polymerization (FIG. 30). Overall, these results show that in vivo delivery of the $\gamma^{377-395}$ peptide reduces the progression and severity of EAE by specifically targeting microglia/macrophage activation in the CNS parenchyma without adverse hemorrhagic effects.

The present inventor has identified inhibition of fibrin/Mac-1 interactions as a novel strategy for the attenuation of the microglia/macrophage activation in the CNS. Histopathological studies in acute MS have identified perivenous lesions that appear to be driven by activated microglia/macrophages sometimes in the absence of lymphocytes (52, 53). Although the activation of microglia and macrophages play a central role in the pathogenesis of MS (3, 4, 43, 53), agents that inhibit the microglia/macrophage response have not been developed (54). Although MS is a disease with profound lesion heterogeneity, BBB disruption and microglia activation is a common feature for the four different subtypes of MS lesions (1). Therefore, targeting fibrin/Mac-1 interactions can be beneficial in different MS subtypes as a microglia-suppressive therapy and could be used in combinational therapies targeting other aspects of MS pathogenesis. In addition to MS, microglia activation is observed in a variety of neurodegenerative diseases characterized by BBB disruption, such as spinal cord injury, stroke and Alzheimer's disease (16). Therefore, targeting fibrin/Mac-1 interactions represents a strategy for inhibiting microglia activation in neurodegenerative diseases. Since blocking fibrin/Mac-1 interactions does not interfere with the physiological properties of fibrin in blood coagulation, this strategy can be applied in chronic diseases such as MS, without hemorrhagic side effects.

The data obtained from the cell culture assays and animal studies can be used in formulating a range of dosages for use in humans and other mammals. The dosage of such compounds lies preferably within a range of circulating plasma or other bodily fluid concentrations that include the ED$_{50}$ with little or no toxicity. The dosage may vary within this range depending upon the dosage form employed and the route of administration utilized. For any compound of the invention, the therapeutically effective dose can be estimated initially from cell culture assays. A dosage may be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful dosages in humans and other mammals. Compound levels in plasma may be measured, for example, by high performance liquid chromatography.

The amount of a compound that may be combined with a pharmaceutically acceptable carrier to produce a single dosage form will vary depending upon the host treated and the particular mode of administration. It will be appreciated by those skilled in the art that the unit content of a compound contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage regime for treating a disease or condition with the compounds of the invention is selected in accordance with a variety of factors, including the type, age, weight, sex, diet and medical condition of the patient, the route of administration, pharmacological considerations such as activity, efficacy, pharmacokinetic and toxicology profiles of the particular compound employed, whether a compound delivery system is utilized and whether the compound is administered as a pro-drug or part of a drug combination. Thus, the dosage regime actually employed may vary widely from subject to subject.

The compounds/polypeptides of the present invention may be formulated by known methods for administration to a subject using several routes which include, but are not limited to, parenteral, oral, topical, intradermal, intramuscular, intraperitoneal, intravenous, subcutaneous, intranasal, epidural, intercranial, and ophthalmic routes. The individual compounds may also be administered in combination with one or more additional compounds of the present invention and/or together with other biologically active or biologically inert agents. Such biologically active or inert agents may be in fluid or mechanical communication with the compound(s) or attached to the compound(s) by ionic, covalent, Van der Waals, hydrophobic, hydrophillic or other physical forces. It is preferred that administration is localized in a subject, but administration may also be systemic.

The compounds of the present invention may be formulated by any conventional manner using one or more pharmaceutically acceptable carriers and/or excipients. Thus, the compounds and their pharmaceutically acceptable salts and solvates may be specifically formulated for administration, e.g., by inhalation or insufflation (either through the mouth or the nose) or oral, buccal, parenteral or rectal administration. The compounds may take the form of charged, neutral and/or other pharmaceutically acceptable salt forms. Examples of pharmaceutically acceptable carriers include, but are not limited to, those described in REMINGTON'S PHARMACEUTICAL SCIENCES (A. R. Gennaro, Ed.), 20th edition, Williams & Wilkins PA, USA (2000).

The compounds may also take the form of solutions, suspensions, emulsions, tablets, pills, capsules, powders, controlled- or sustained-release formulations and the like. Such formulations will contain a therapeutically effective amount of the compound, preferably in purified form, together with a suitable amount of carrier so as to provide the form for proper administration to the patient. The formulation should suit the mode of administration.

The compound may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The formulation may take such forms as suspensions, solutions or emulsions in oily or aqueous vehicles, and may contain formulatory agents such as suspending, stabilizing and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the parenteral preparation.

Alternatively, the compound may be formulated in powder form for constitution with a suitable vehicle, such as sterile pyrogen-free water, before use. For example, a compound suitable for parenteral administration may comprise a sterile isotonic saline solution containing between 0.1 percent and 90 percent weight per volume of the compound. By way of example, a solution may contain from about 0.1 percent to about 20 percent, more preferably from about 0.55 percent to about 17 percent, more preferably from about 0.8 to about 14 percent, and still more preferably about 10 percent of the compound. The solution or powder preparation may also include a solubilizing agent and a local anesthetic such as lignocaine to ease pain at the site of the injection. Other methods of parenteral delivery of compounds will be known to the skilled artisan and are within the scope of the invention.

For oral administration, the compound may take the form of tablets or capsules prepared by conventional means with pharmaceutically acceptable excipients such as binding agents, fillers, lubricants and disintegrants:

The tablets or capsules may optionally be coated by methods well known in the art. If binders and/or fillers are used with the compounds of the invention, they are typically formulated as about 50 to about 99 weight percent of the compound. In one aspect, about 0.5 to about 15 weight percent of disintegrant, and particularly about 1 to about 5 weight percent of disintegrant, may be used in combination with the compound. A lubricant may optionally be added, typically in an amount of less than about 1 weight percent of the compound. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other less typical formulations are known in the art.

Liquid preparations for oral administration may take the form of solutions, syrups or suspensions. Alternatively, the liquid preparations may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations may also contain buffer salts, flavoring, coloring, perfuming and sweetening agents as appropriate. Preparations for oral administration may also be formulated to achieve controlled release of the compound. Oral formulations preferably contain 10% to 95% compound. In addition, the compounds of the present invention may be formulated for buccal administration in the form of tablets or lozenges formulated in a conventional manner. Other methods of oral delivery of compounds will be known to the skilled artisan and are within the scope of the invention.

Controlled-release (or sustained-release) preparations may be formulated to extend the activity of the compound and reduce dosage frequency. Controlled-release preparations can also be used to effect the time of onset of action or other characteristics, such as blood levels of the compound, and consequently affect the occurrence of side effects.

Controlled-release preparations may be designed to initially release an amount of a compound that produces the desired therapeutic effect, and gradually and continually release other amounts of the compound to maintain the level of therapeutic effect over an extended period of time. In order to maintain a near-constant level of a compound in, the body, the compound can be released from the dosage form at a rate that will replace the amount of compound being metabolized and/or excreted from the body. The controlled-release of a compound may be stimulated by various inducers, e.g., change in pH, change in temperature, enzymes, water, or other physiological conditions or molecules.

Controlled-release systems may include, for example, an infusion pump which may be used to administer the compound in a manner similar to that used for delivering insulin or chemotherapy to specific organs or tumors. Typically, using such a system, the compound is administered in combination with a biodegradable, biocompatible polymeric implant that releases the compound over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

The compounds of the invention may be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds will be known to the skilled artisan and are within the scope of the invention.

The compound may also be formulated as a depot preparation. Such long-acting formulations may be administered by implantation (e.g., subcutaneously or intramuscularly or intercranially) or by injection. Accordingly, the compounds may be formulated with suitable polymeric or hydrophobic materials such as an emulsion in an acceptable oil or ion exchange resins, or as sparingly soluble derivatives such as a sparingly soluble salt. Other methods of depot delivery of compounds will be known to the skilled artisan and are within the scope of the invention.

Various other delivery systems are known in the art and can be used to administer the compounds of the invention. Moreover, these and other delivery systems may be combined and/or modified to optimize the administration of the compounds of the present invention. Exemplary formulations using the compounds of the present invention are described below (the compounds of the present invention are indicated as the active ingredient, but those of skill in the art will recognize that pro-drugs and compound combinations are also meant to be encompassed by this term):

In various embodiments, the present invention can also involve kits. Such kits can include the compounds/polypeptides/antibodies of the present invention and, in certain embodiments, instructions for administration. When supplied as a kit, different components of a compound formulation can be packaged in separate containers and admixed immediately before use. Such packaging of the components separately can, if desired, be presented in a pack or dispenser device which may contain one or more unit dosage forms containing the compound/polyepeptide. The pack may, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

Kits may also include reagents in separate containers such as, for example, sterile water or saline to be added to a lyophilized active component packaged separately. For example, sealed glass ampules may contain lyophilized polypeptide and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit, or supplied as electronic mail.

The identified compounds treat, inhibit, control and/or prevent, or at least partially arrest or partially prevent, nervous system disorders and can be administered to a subject at therapeutically effective doses for the inhibition, prevention, prophylaxis or therapy. The compounds of the present invention comprise a therapeutically effective dosage of a polypeptide, a term which includes therapeutically, inhibitory, preventive and prophylactically effective doses of the compounds of the present invention and is more particularly defined above. Without being bound to any particular theory, applicants surmise that these pharmaceutical compounds are effective in treatment when administered to a subject suffering from a nervous system disorder. The subject is preferably an animal, including, but not limited to, mammals, reptiles and avians, more preferably horses, cows, dogs, cats, sheep, pigs, and chickens, and most preferably human.

"Antagonist" includes any molecule that partially or fully blocks, inhibits, or neutralizes a biological activity of endogenous Mac-1. Similarly, "agonist" includes any molecule that mimics a biological activity of endogenous Mac-1. Molecules that can act as agonists or antagonists include Abs or Ab fragments, fragments or variants of endogenous Mac-1, peptides, antisense oligonucleotides, small organic molecules, etc.

To assay for antagonists, Mac-1 is added to, or expressed in, a cell along with the compound to be screened for a particular activity. If the compound inhibits the activity of interest in the presence of the Mac-1, that compound is an antagonist to the Mac-1; if Mac-1 activity is enhanced, the compound is an agonist.

Mac-1-expressing cells can be easily identified using any of the disclosed methods. For example, antibodies that recognize the amino- or carboxy-terminus of human Mac-1 can be used to screen candidate cells by immunoprecipitation, Western blots, and immunohistochemical techniques, or flow cytometry.

Screening techniques well known to those skilled in the art can identify Mac-1 agonist or antagonist molecules. Examples of antagonists and agonists include: (1) small organic and inorganic compounds, (2) small peptides, (3) Abs and derivatives, (4) polypeptides closely related to Mac-1, (5) antisense DNA and RNA, (6) ribozymes, (7) triple DNA helices, (8) siRNAs and (9) nucleic acid aptamers.

Small molecules that bind to the Mac-1 active site or other relevant part of the polypeptide and inhibit the biological activity of the Mac-1 are antagonists. Examples of small molecule antagonists include small peptides, peptide-like molecules, preferably soluble, and synthetic non-peptidyl organic or inorganic compounds. These same molecules, if they enhance Mac-1 activity, are examples of agonists.

Almost any antibody that affects Mac-1's function can be a candidate antagonist or agonist. Examples of antibody antagonists include polyclonal, monoclonal, single-chain, anti-idiotypic, chimeric Abs, or humanized versions of such Abs or fragments. Abs may be from any species in which an immune response can be raised. Humanized Abs are also contemplated.

Alternatively, a potential antagonist or agonist may be a closely related protein, for example, a mutated form of the Mac-1 that recognizes a Mac-1-interacting protein but imparts no effect, thereby competitively inhibiting Mac-1 action. Alternatively, a mutated Mac-1 may be constitutively activated and may act as an agonist.

"Percent (%) amino acid sequence identity" is defined as the percentage of amino acid residues that are identical with amino acid residues in the disclosed polypeptide sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\text{\% amino acid sequence identity} = X/Y \cdot 100$$

where X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

Biologically active portions of fibrin/fibrinogen may have an amino acid sequence shown in SEQ ID NO: 1, or substantially homologous to SEQ ID NO: 1, and retains the functional activity of the protein of SEQ ED NO: 1, yet differs in amino acid sequence due to natural allelic variation or mutagenesis. Other biologically active proteins comprise an amino acid sequence at least about 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to the amino acid sequence of SEQ ID NO: 1 and retains the functional activity of SEQ ID NO:1.

Such proteins which retain the functional activity of SEQ ID NO: 1 can include peptidomimetics. Thus, the invention also provides for reduction of a polypeptide having SEQ ID NO: 1 to generate mimetics, e.g. peptide or non-peptide agents, that are able to disrupt binding of Mac-1 to other proteins or molecules with which the native Mac-1 protein interacts. Thus, the techniques described herein can also be used to map which determinants of fibrin/fibrinogen protein participate in the intermolecular interactions involved in, e.g., binding of fibrin/fibrinogen protein to other proteins which may function upstream (e.g., activators or repressors of fibrin/fibrinogen functional activity) of the fibrin/fibrinogen protein or to proteins or nucleic acids which may function downstream of the fibrin/fibrinogen protein, and whether such molecules are positively or negatively regulated by the fibrin/fibrinogen protein. To illustrate, the critical residues of an fibrin/fibrinogen protein which are involved in molecular recognition of, e.g., fibrin/fibrinogen protein or other components upstream or downstream of the fibrin/fibrinogen protein can be determined and used to generate fibrin/fibrinogen protein-derived peptidomimetics which competitively inhibit binding of the fibrin/fibrinogen protein to that moiety. By employing scanning mutagenesis to map the amino acid residues of a fibrin/fibrinogen protein that are involved in binding other extracellular proteins, peptidomimetic compounds can be generated which mimic those residues of a native fibrin/fibrinogen protein. Such mimetics may then be used to interfere with the normal function of an fibrin/fibrinogen protein.

For example, non-hydrolyzable peptide analogs of such residues can be generated using benzodiazepine (see, e.g., Freidinger et al. in Peptides: Chemistry and Biology, G. R. Marshall ed., ESCOM Publisher. Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopepitides (Ewenson et al.

(1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1: 1231), and beta-aminoalcohols (Gordon et al. (1985) Biochem. Biophys. Res. Commun. 126:419; and Dann et al. (1986) Biochem. Biophys. Res. Commun. 134:71) fibrin/fibrinogen proteins may also be chemically modified to create fibrin/fibrinogen protein derivatives by forming covalent or aggregate conjugates with other chemical moieties, such as glycosyl groups, lipids, phosphate, acetyl groups and the like. Covalent derivatives of fibrin/fibrinogen protein can be prepared by linking the chemical moieties to functional groups on amino acid side chains of the protein or at the N-terminus or at the C-terminus of the polypeptide.

Anti-Mac-1 Abs may further comprise humanized or human Abs. Humanized forms of non-human Abs are chimeric Igs, Ig chains or fragments (such as $F_v$, $F_{ab}$, $F_{ab'}$, $F_{(ab')2}$ or other antigen-binding subsequences of Abs) that contain minimal sequence derived from non-human Ig.

Generally, a humanized antibody has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human antibody. Such "humanized" Abs are chimeric Abs, wherein substantially less than an intact human variable domain has been substituted by the corresponding sequence from a non-human species. In practice, humanized Abs are typically human Abs in which some CDR residues and possibly some FR residues are substituted by residues from analogous sites in rodent Abs. Humanized Abs include human Igs (recipient antibody) in which residues from a complementary determining region (CDR) of the recipient are replaced by residues from a CDR of a non-human species (donor antibody) such as mouse, rat or rabbit, having the desired specificity, affinity and capacity. In some instances, corresponding non-human residues replace framework residues of the human Ig. Humanized Abs may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region ($F_c$) typically that of a human Ig.

Human Abs can also be produced using various techniques, including phage display libraries and the preparation of human mAbs. Similarly, introducing human Ig genes into transgenic animals in which the endogenous Ig genes have been partially or completely inactivated can be exploited to synthesize human Abs. Upon challenge, human antibody production is observed, which closely resembles that seen in humans in all respects, including gene rearrangement, assembly, and antibody repertoire.

Bi-specific Abs are monoclonal, preferably human or humanized, that have binding specificities for at least two different antigens. For example, a binding specificity is Mac-1; the other is for any antigen of choice, preferably a cell-surface protein or receptor or receptor subunit. Traditionally, the recombinant production of bi-specific Abs is based on the co-expression of two Ig heavy-chain/light-chain pairs, where the two heavy chains have different specificities. Because of the random assortment of Ig heavy and light chains, the resulting hybridomas (quadromas) produce a potential mixture of ten different antibody molecules, of which only one has the desired bi-specific structure. The desired antibody can be purified using affinity chromatography or other techniques.

To manufacture a bi-specific antibody, variable domains with the desired antibody-antigen combining sites are fused to Ig constant domain sequences. The fusion is preferably with an Ig heavy-chain constant domain, comprising at least part of the hinge, CH2, and CH3 regions. Preferably, the first heavy-chain constant region (CH1) containing the site necessary for light-chain binding is in at least one of the fusions. DNAs encoding the Ig heavy-chain fusions and, if desired, the Ig light chain, are inserted into separate expression vectors and are co-transfected into a suitable host organism.

The interface between a pair of antibody molecules can be engineered to maximize the percentage of heterodimers that are recovered from recombinant cell culture. The preferred interface comprises at least part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This mechanism increases the yield of the heterodimer over unwanted end products such as homodimers.

Bi-specific Abs can be prepared as full length Abs or antibody fragments (e.g., $F_{(ab')2}$ bi-specific Abs). One technique to generate bi-specific Abs exploits chemical linkage. Intact Abs can be proteolytically cleaved to generate $F_{(ab')2}$ fragments. Fragments are reduced with a dithiol complexing agent, such as sodium arsenite, to stabilize vicinal dithiols and prevent intermolecular disulfide formation. The generated $F_{ab'}$ fragments are then converted to thionitrobenzoate (TNB) derivatives. One of the $F_{ab'}$-TNB derivatives is then reconverted to the $F_{ab'}$-thiol by reduction with mercaptoethylamine and is mixed with an equimolar amount of the other $F_{ab'}$-TNB derivative to form the bi-specific antibody. The produced bi-specific Abs can be used as agents for the selective immobilization of enzymes.

$F_{ab'}$ fragments may be directly recovered from E. coli and chemically coupled to form bi-specific Abs. For example, fully humanized bi-specific $F_{(ab')2}$ Abs can be produced by methods known to those of skill in the art. Each $F_{ab'}$ fragment is separately secreted from E. coli and directly coupled chemically in vitro, forming the bi-specific antibody.

Various techniques for making and isolating bi-specific antibody fragments directly from recombinant cell culture have also been described. For example, leucine zipper motifs can be exploited. Peptides from the Fos and Jun proteins are linked to the $F_{ab'}$ portions of two different Abs by gene fusion. The antibody homodimers are reduced at the hinge region to form monomers and then re-oxidized to form antibody heterodimers. This method can also produce antibody homodimers. The "diabody" technology provides an alternative method to generate bi-specific antibody fragments. The fragments comprise a heavy-chain variable domain ($V_H$) connected to a light-chain variable domain ($V_L$) by a linker that is too short to allow pairing between the two domains on the same chain. The $V_H$ and $V_L$ domains of one fragment are forced to pair with the complementary $V_L$ and $V_H$ domains of another fragment, forming two antigen-binding sites. Another strategy for making bi-specific antibody fragments is the use of single-chain $F_v$ (s$F_v$) dimers. Abs with more than two valences are also contemplated, such as tri-specific Abs.

Abs of the invention, including polyclonal, monoclonal, humanized and fully human Abs, can be used therapeutically. Such agents will generally be employed to treat or prevent a disease or pathology in a subject. An antibody preparation, preferably one having high antigen specificity and affinity generally mediates an effect by binding the target epitope(s). Generally, administration of such Abs may mediate one of two effects: (1) the antibody may prevent ligand binding, eliminating endogenous ligand binding and subsequent signal transduction, or (2) the antibody elicits a physiological result by binding an effector site on the target molecule, initiating signal transduction.

A therapeutically effective amount of an antibody relates generally to the amount needed to achieve a therapeutic objective, epitope binding affinity, administration rate, and depletion rate of the antibody from a subject. Common ranges for therapeutically effective doses may be, as a nonlimiting example, from about 0.1 mg/kg body weight to about 50 mg/kg body weight. Dosing frequencies may range, for example, from twice daily to once a week.

Anti-Mac-1 interacting molecules (such as aptamers) identified in other assays, can be administered in pharmaceutical compositions as disclosed, infra, to treat various disorders. Abs that are internalized are preferred when whole Abs are used as inhibitors. Liposomes may also be used as a delivery vehicle for intracellular introduction. Where antibody fragments are used, the smallest inhibitory fragment that specifically binds to the epitope is preferred. For example, peptide molecules can be designed that bind a preferred epitope based on the variable-region sequences of a useful antibody. Such peptides can be synthesized chemically and/or produced by recombinant DNA technology. Formulations may also contain more than one active compound for a particular treatment, preferably those with activities that do not adversely affect each other. The composition may comprise an agent that enhances function, such as a cytotoxic agent, cytokine, chemotherapeutic agent, or growth-inhibitory agent.

The active ingredients can also be entrapped in microcapsules prepared by coacervation techniques or by interfacial polymerization; for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles, and nanocapsules) or in macroemulsions. The formulations to be used for in vivo administration are highly preferred to be sterile. This is readily accomplished by filtration through sterile filtration membranes or any of a number of techniques.

Sustained-release preparations may also be prepared, such as semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as injectable microspheres composed of lactic acid-glycolic acid copolymer, and poly-D-(-)-3-hydroxybutyric acid. While polymers such as ethylene-vinyl acetate and lactic acid-glycolic acid enable release of molecules for over 100 days, certain hydrogels release proteins for shorter time periods and may be preferred.

EXAMPLES

Aspects of the present teachings may be further understood in light of the following examples, which should not be construed as limiting the scope of the present teachings in any way. Materials and methods used in the examples include the following:

Animals. Female SJL/J and C57BL/6 mice (6 weeks old) were purchased from the Jackson Laboratory (Bar Harbor, Me.) or Harlan Sprague Dawley (Indianapolis, Ind.). Female Fibγ$^{390-396A}$ mice (6 weeks old) were generated from double heterozygous matings to produce homozygous Fibγ$^{396-396A}$ mice (15) and Fibγ$^{WT}$ littermate mice as controls. Fibγ$^{390-396A}$ mice were backcrossed six generations to C57Bl/6 mice (15).

Induction of EAE. EAE was induced in 6 week old female SJL/J or C57BL/6 mice by subcutaneous immunization with 150 µg PLP$_{139-151}$ (HSLGKWLGHPDKF) (SEQ ID NO: 5). American Peptide Company and Azco Pharmchem, San Jose, Calif.) or 50 µg MOG$_{35-55}$ (MEVGWYRSPFSRVVH-LYRDGK) (SEQ ID NO: 6), Sigma-Aldrich, St. Louis, Mo.) in complete Freund's adjuvant (Sigma-Aldrich, St. Louis, Mo.) supplemented with 200 ng heat inactivated *mycobacterium tuberculosis* H37Ra (Difco Laboratories, Detroit, Mich.). Mice were injected intravenously with 200 ng pertussis toxin (Sigma-Aldrich, St. Louis, Mo.) on days 0 and 2 of the immunization. Mice were scored daily. 0: no symptoms, 1: loss of tail tone, 2: ataxia, 3: hindlimb paralysis, 4: hindlimb and forelimb paralysis, 5: moribund Data are represented as the mean clinical score and are mean±SEM. Statistical calculations were made by using Student's t test.

Systemic defibrinogenation. Mice were depleted of fibrinogen as described (55). The pumps deliver 0.5 µl/hour, thus the mice received 2.4 U ancrod/day. In control animals, buffer-filled mini-pumps were implanted.

Fibrinogen γ$^{377-395}$ peptide vaccination. Vaccination was performed as described (56) with the following modifications. Five week old female SJL/J mice were immunized with 200 µg fibrinogen γ$^{377-395}$ peptide (YSMKETTMKIIPFN-RLSIG) (SEQ ID NO: 2), Azco Pharmchem, San Jose, Calif.) emulsified with an equal volume of incomplete freund's adjuvant (Sigma-Aldrich, St. Louis, Mo.). Mice were immunized four times in alternating rear flanks over the course of two weeks. Control animals were immunized with incomplete Freund's adjuvant.

Intranasal γ$^{377-395}$ peptide administration. Fibrinogen γ$^{377-395}$ peptide (YSMKETTMKIIPFNRLSIG) (SEQ ID NO: 2), Azco Pharmchem, San Jose, Calif.) was resuspended in 0.9% NaCl at a concentration of 3 mg/mL. Peptides were aliquoted as single doses and stored at 20° C. Mice were administered 5 µL of peptide or 0.9% NaCl, as a control, in each nare daily using a P10 micropipettor (Gilson, Middleton, Wis.) beginning after the peak of the first paralytic episode.

Histopathology. Histopathologic analysis and quantification of inflammation and demyelination in mouse tissue was performed on cryostat or paraffin sections as described (57). Sections were stained with luxol fast blue and nuclear red. Spinal cord sections were fixed with 2% PFA for 10 minutes at 4° C. and immunostained with a sheep anti-fibrinogen antibody (1:200, US Biological, Swampscott, Mass.), rat anti-CD11b (1:5, Chemicon), von Willebrand Factor (1:1000, Dakocytomation, Glostrup, Denmark), iNOS (polyclonal Chemicon, Temecula, Calif., 1:750), Mac-3 (rat-anti-mouse, Pharmingen, San Diego, Calif., 1:200), CNPase (monoclonal, Sternberger monoclonals, Lutherville, Md., 1:2000). For human MS, paraffin embedded material was obtained from the Archives of the Center for Brain Research, Medical University of Vienna. Double immunofluorescence was performed with antibodies against CD68 and fibrin. Images were collected using an Axioplan 2 Zeiss microscope with an Axiocam HRc camera or were processed for confocal microscopy using Olympus and Zeiss confocal microscopes.

Rotarod behavior test. The rotarod assay was performed on a TSE accelerating Rotarod apparatus (TSE Technical and Scientific Equipment GmbH) as described (58). Rotarod assays were conducted with a 300 second maximum time limit and means were collected for at least three trials. Statistical calculations were made by using Students t test.

Culture of primary microglia cells. Microglia were isolated from cultures of mixed cortical cells as described (59). In brief, cortices from P1 mice were isolated and digested with trypsin (0.4%) for 20 minutes at 37° C. Cells from 4 pups were plated onto PDL-coated 75 cm2 tissue-culture flasks. The culture medium (DMEM, 10% heat-inactivated FBS, and 1% Pen/Strep) was changed on day 2. After 2-3 weeks in culture, the microglia were removed by the addition of 12 mM lidocaine (Sigma-Aldrich, St. Louis, Mo.) and orbital shaking (180 rpm) for 20 minutes at 37° C. The cells were centrifuged (350×G) and the pellet was resuspended in complete medium and plated onto PDL-coated tissue culture dishes. Microglia cell cultures were >95% pure as determined with three different markers, IsoB4, IBA-1 and CD11b. To immobilize fibrinogen, tissue culture dishes were incubated overnight with 50 µg/mL fibrinogen (Calbiochem, San Diego, Calif.) in 20 mM Tris (pH 7.5) and 0.1 M NaCl at 37° C. for all fibrinogen treatments. To serve as positive controls, LPS (Sigma-Aldrich, St. Louis, Mo.) was added to the media at 1 µg/mL.

Phagocytosis assay. Phagocytosis assays were performed on both primary murine microglia and a murine microglia cell line (BV2). BV2 cells are an established cell line used to study microglia responses (46). BV2 cells were routinely passaged in DMEM, 20% heat inactivated FBS, and 1% Pen/Strep. Microglia phagocytosis was assessed using the Vybrant phagocytosis assay kit (Molecular Probes, Eugene, Oreg.) according to the manufacturer's recommendations. Microglia were cultured in 96-well plates at 5,000 cells/well for 36 hours at 37° C. Blocking experiments included the addition of LY294002 (1 µM, Cell Signaling, Beverly, Mass.), rat anti-CD11b (10 mg/mL, eBioscience, San Diego, Calif.), rat anti-TLR4 (10 µg/mL, eBioscience, San Diego, Calif.) or rat IgG (10 µg/mL, Jackson ImmunoResearch Laboratories, West Grove, Pa.) to the media. Results were obtained from four separate experiments performed in triplicates. Statistical calculations were made by using Student's t-test.

Morphometry. Primary microglia were used for all morphologic analysis. Cells were plated on coated fibrinogen or in the presence of LPS for 72 hours. Microglia were fixed with methanol and immunostained with Isolectin B4 (1:300, Sigma-Aldrich, St. Louis, Mo.). Activated microglia were quantificated as those cells larger than 2,000 µm$^2$. Blocking experiments involved the daily administration of rat anti-CD11b (10 µg/mL, eBioscience, San Diego, Calif.), $\gamma^{377-395}$ peptide (200 µM) or rat IgG (10 µg/mL, Jackson ImmunoResearch Laboratories, West Grove, Pa.). Results were obtained from six separate experiments performed in duplicates. 250 cells per condition were counted for each individual experiment. Statistical calculations were made by using Student's t test.

Endotoxin detection assay. Fibrinogen samples were tested for contaminating endotoxins by a Limulus Amebocyte Lysate assay (E-TOXATE kit; Sigma-Aldrich, St. Louis, Mo.). Fibrinogen-treated samples had undetectable endotoxin levels (<0.5 endotoxin units).

Immunoblots. Western blots were performed using standard protocols (55). Microglia were serum-starved overnight and plated on fibrinogen or with LPS for 6 hours. Lysates were electrophoresed on 4-12% gradient SDS-PAGE gels and probed with phospho and total Akt antibodies (1:1000, Cell Signaling, Beverly, Mass.). RhoA activation was performed as described (60). Briefly, 2×107 microglia were plated on fibrinogen for 6 hours or with LPS for 10 minutes. Cell lysates were incubated with GST-Rhotekin agarose beads (kindly provided by Dr. Joan Heller Brown, UCSD) for 45 minutes at 4° C. The beads were washed, resuspended in Laemmli sample buffer, and electophoresed on a 15% SDS-PAGE gel. Activated and total Rho were detected with mouse anti-RhoA (1:500, Santa Cruz Biotechnology, Santa Cruz, Calif.). Densitometry was performed using the NIH Scion Image software using three blots from three separate experiments.

Deconvolution microscopy. Fluorescent images were obtained as described (60). Primary microglia were stimulated with fibrinogen as described above. Cells were immunostained with antibodies to total actin (1:100, Sigma-Aldrich, St. Louis, Mo.) or β-tubulin (1:100, Sigma-Aldrich, St. Louis, Mo.).

Isolation of mouse splenocytes and T cell proliferation assay. Spleens were removed from control and fibrin-depleted mice after induction of $PLP_{139-151}$ EAE and washed in PBS. Spleens were mechanically dissociated with sterile blades and filtered through 70 µm nylon screens. Splenocytes were pelleted and washed with an erythrocyte lysing solution (Biolegend, San Diego, Calif.). Cells were washed twice with PBS, counted and seeded at a density of 0.5×10$^6$ cells/96-well. Cells from both control and fibrin-depleted mice were either untreated or stimulated with 20 µg/mL $PLP_{139-151}$ and proliferation was assayed by BrdU incorporation (Roche Applied Sciences, Indianapolis, Ind.) according to the manufacturer's instructions.

FACS Analysis. Primary mouse splenocytes were isolated from control and $\gamma^{377-395}$ peptide-treated mice, immunized with PLP139-151, on day 29 after immunization. Cells were immunostained with antibodies to CD4, CD8, CD11b, CD11c, CD19, B220 (1:100, Biolegend, San Diego, Calif.) and analyzed on a Becton Dickinson FACSCalibur flow cytometer.

Hematological Analyses. Citrated plasma was prepared from mice administered intranasally 30 µg or 90 µg of $\gamma^{377-395}$ peptide or saline control daily for seven days. Plasma clotting times were measured by combining 10 µl of citrated plasma with 10 µl of 2 U/ml bovine thrombin (Enzyme Research Laboratories, South Bend, Ind., USA) and 40 mM. $CaCl_2$ in a weigh boat floating in a 37° C. water bath. Time to clot was determined by mixing with a toothpick. Plasma thrombin times were established as described previously (15). Fibrin polymerization was evaluated by standard turbidity assays using plasma. Briefly, citrate plasma (diluted tenfold in 20 mM HEPES, pH 7.4, containing 0.15 M NaCl and 5 mM-amino caproic acid) was combined with bovine thrombin (final concentration 0.2 U/ml; Enzyme Research Laboratories, South Bend, Ind., USA), and $Ca^{2+}$ (10 mM), and $OD_{350}$ measurements were taken every 30 seconds.

Example 1

Figure 1:
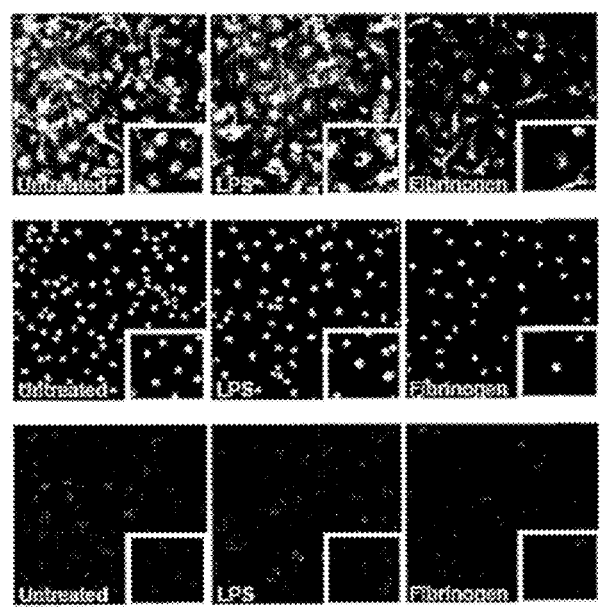
Figure 2:
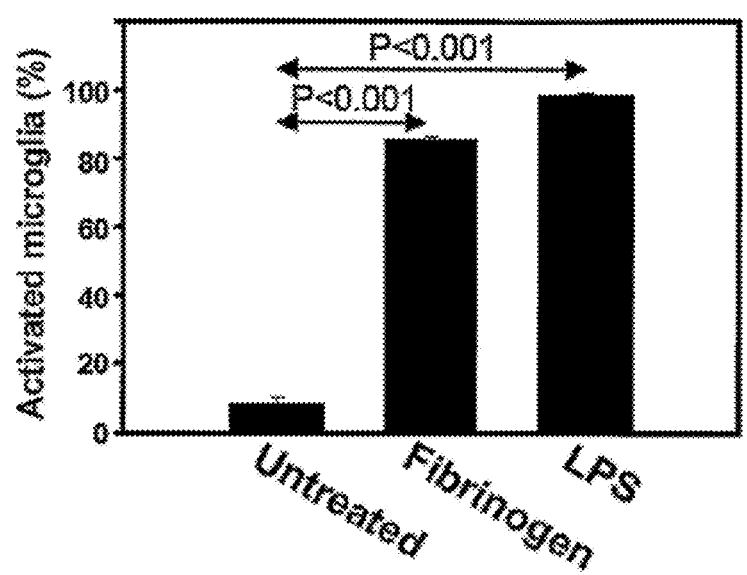
FIG. 2 illustrates Quantification of microglia activation. The data reveals a dramatic increase upon fibrinogen stimulation.
Figure 3:
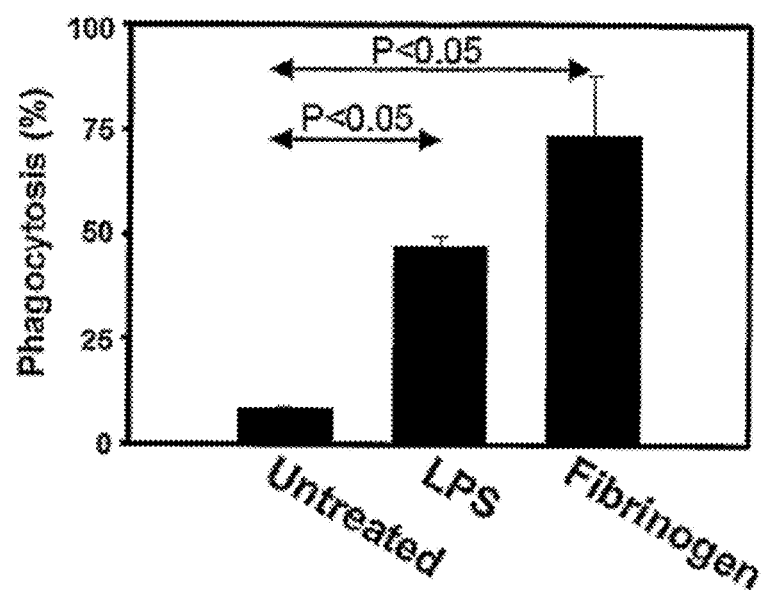
FIG. 3 depicts fibrinogen stimulated microglia showed increased phagocytosis of fluorescent E. coli as compared to untreated microglia. LPS served as a positive control.

This example illustrates that fibrinogen directly activates microglia, resulting in cytoskeletal rearrangement and increased phagocytosis. Fibrinogen directly activates microglia resulting in cytoskeletal rearrangements and increased phagocytosis. In this example, we first tested the effects of fibrinogen on pure primary microglia cells. Immobilized fibrinogen had a dramatic effect on microglia activation characterized by an increase in cell size (FIG. 1, right column), when compared to untreated controls (FIG. 1, left column). Quantification revealed a 85.5±1.4% of activated microglia after fibrinogen treatment vs. 8.2±3.4% in untreated cells (FIGS. 5-10; P<0.001). By contrast to immobilized fibrinogen, soluble fibrinogen did not induce changes in microglia morphology (data not shown). Lipopolysaccharide (LPS) was used as a positive control (FIGS. 1-10). Using an endotoxin determination assay, we verified that there was no LPS contamination in the fibrinogen-treated cultures. To assess the functional effect of this morphologic activation, we performed phagocytosis assays. Fibrinogen stimulation resulted in a 65.3% increase in phagocytosis as compared to untreated controls (P<0.05), while LPS incubation, by comparison, increased phagocytosis by 39.1% (P<0.05) (FIGS. 11-13). Previous studies have demonstrated that dynamic rearrangements of both the actin (26) and microtubule (27) networks are critical for phagocytosis. Deconvolution microscopy showed that fibrinogen stimulation resulted in dramatic rearrangement of the microglial cytoskeleton as determined by immunostaining of actin and (β-tubulin (FIGS. 14-19). Overall, these results indicate that fibrinogen induces microglia differentiation into a phagocytic state.

Example 2

This example illustrates that fibrinogen can activate microglia via the Mac-1 integrin receptor Mac-1 orchestrates the innate immune response, by regulating phagocyte adhesion, migration, and engulfment of complement-opsonized particles (28). M1/70, an antibody which blocks binding of fibrinogen to CD11b (24, 29), inhibited fibrin-mediated microglia activation (FIGS. 20-22). Quantification showed 71±4.9% of activated microglia in fibrinogen treated cells vs. 18±0.7% in cells treated with fibrinogen in the presence of M1/70 (FIGS. 23-27, P<0.01). The inhibitory effect of M1/70 was specific for fibrinogen and did not affect LPS-mediated activation of microglia (FIG. 6). Moreover, blocking CD11b reduced phagocytosis of fibrinogen-treated cells by 40% (P<0.05) (FIGS. 28-30). Previous studies have established that the Toll-like Receptor-4 (TLR4) LPS receptor mediates LPS-induced microglia activation (30, 31). By contrast, blocking TLR-4 did not affect fibrinogen-mediated phagocytosis, suggesting that Mac-1 was the major receptor to induce fibrinogen-mediated phagocytosis (FIGS. 28-30).

Example 3

This example illustrates fibrinogen induces increases in RhoA and Akt phosphorylation in microglia. RhoA and PI3K are the two major signaling pathways downstream of Mac-1 that mediate the cytoskeletal rearrangements for the induction of phagocytosis (28, 32, 33). Fibrinogen applied as described above induced a 1.9-fold increase of active RhoA and a 24-fold increase in Akt phosphorylation in microglia (FIG. 31). Furthermore, blocking the PI3K signaling pathway using LY294002, inhibited the fibrin-induced increase of phagocytosis in microglia (FIGS. 28-30, P<0.01), suggesting that PI3K is downstream of fibrin/Mac-1 signaling in microglia cells. This is the first evidence suggesting that fibrinogen can induce Mac-1-dependent signaling in microglia.

Example 4

This example illustrates induction of phagocytosis in microglia. Analysis of demyelinated spinal cords after induction of $PLP_{139-151}$ experimental autoimmune encephalomyelitis (EAE) in mice showed that CD11b-positive microglia (FIG. 9, top right panel), were surrounded by fibrin (FIG. 9, top left panel). Similarly, analysis of acute demyelinating lesions of human MS showed that fibrin (FIG. 10, middle panel) surrounded activated microglia cells (FIG. 10, top panel). Overall these results show that fibrinogen/CD11b signaling induces phagocytosis in microglia and demonstrate both in EAE and in human MS the presence of this ligand/receptor system on active microglia within inflammatory demyelinating lesions.

Example 5

This example illustrates that fibrin depletion inhibits microglia activation in vivo and attenuates inflammatory demyelination. In this example, we further examined whether fibrin is required for the activation of Mac-1 positive cells in vivo. In these experiments, we administered the anticoagulant ancrod (34) in an established remitting-relapsing model of $PLP_{139-151}$ EAE (35) after the development of the first paralytic incidence. At the time of the first relapse, untreated mice show dramatic activation of CD11b-positive cells characterized by thick processes (FIG. 11, left column). By contrast, in ancrod-treated mice CD11b-positive cells appear with ramified morphology (FIG. 11, right column) resembling CD11b-positive cells in the normal spinal cord (FIG. 32). Single channel images are shown in FIG. 32. Untreated mice showed extensive inflammatory demyelinating lesions in the cerebellum (FIG. 33, asterisk) and spinal cord (FIG. 33, arrows). By contrast, in ancrod-treated mice inflammatory demyelination was dramatically decreased (FIG. 33). Ancrod treatment resulted in decreased demyelination by 7-fold in the cerebellum and by 2-fold in the spinal cord. Splenocytes isolated from untreated and ancrod-treated mice showed no difference in proliferation upon stimulation with $PLP_{139-151}$ (FIG. S4), further suggesting that CD11b-positive cells are the major cell target of fibrin in the nervous system. Fibrin-depleted mice recovered faster from the first paralytic incidence and, in contrast to control mice, never relapsed (FIG. 12). In a rotarod behavioral test, performed before the first relapse of the untreated group, fibrin-depleted mice showed a 3-fold increase of motor strength and coordination when compared to the untreated group (FIG. 13). Overall, these results suggest that fibrin is a major contributor to the local activation of CD11b-positive cells in vivo. In addition, this is the first demonstration that an anti-coagulant may improve clinical symptoms and reduce inflammatory demyelination when administered after the onset of paralytic symptoms.

Example 6

This example illustrates that $Fib\gamma^{390-396A}$ mice have reduced clinical scores and inflammation. To examine the contribution of fibrinogen/Mac-1 signaling in inflammatory demyelination in vivo, we utilized mice with a knock-in mutation of seven amino acids at residues ($N_{390}RLSIGE_{396}$) (SEQ ID NO: 3) to alanine residues ($A_{390}AAAAAA_{396}$) (SEQ ID NO: 4) that abolishes fibrinogen binding to the Mac-1 receptor (15). These mice, termed $Fib\gamma^{390-396A}$ and their age- and sex-matched littermate controls ($Fib\gamma^{WT}$) were in C57Bl/6 background and were immunized with $MOG_{35-55}$ peptide (FIG. 14). $Fib\gamma^{390-396A}$ mice showed an average clinical score of 2.2 (ataxia) at day 17 after immunization, while the $Fib\gamma^{WT}$ mice developed clinical symptoms of paralysis, showing an average score of 3.7 (hind limb paralysis) (P<0.01). In the $Fib\gamma^{WT}$ mouse group 73% of $Fib\gamma^{WT}$ mice (11/15) were paralyzed, by contrast to 24% of $Fib\gamma^{390-396A}$ mice (4/17) (clinical score>3) (FIG. 15), further demonstrating decreased severity of EAE. $Fib\gamma^{390396A}$ mice showed a 1.5-fold increase in motor skills, when compared to $Fib\gamma^{WT}$ mice (Fibγ$^{390-396A}$, 269±9 sec vs. Fibγ$^{WT}$, 169±23 sec, P<0.05) (FIG. 18). Lesions were decreased 3-fold in Fibγ$^{390-396A}$ mice, when compared to Fibγ$^{WT}$ (FIG. 16). In accordance, spinal cord sections showed a decrease of IsoB4-positive cells in Fibγ$^{390-396A}$ mice, when compared to Fibγ$^{WT}$ controls (FIG. 19). Decrease in clinical severity was also observed at later time points after the immunization (FIGS. 14 and 15). In addition, 27% Fibγ$^{WT}$ mice (4/15) died by contrast to only 6% of the Fibγ$^{390-396A}$ mice (1/17) (FIG. 17). Overall, these results suggest that the γ$^{390-396}$ binding site of fibrinogen to Mac-1 regulates the severity of inflammatory demyelination.

Example 7

This example illustrates that the fibrin γ$^{377-395}$ peptide blocks microglia activation in vitro. Both the in vitro (FIGS. 2-10) and in vivo experiments (FIGS. 14-19) show that fibrinogen signaling through the Mac-1 receptor contributes to microglia activation and regulates the severity of inflammatory demyelination in EAE. Biochemical studies identified that the γ$_{377}$YSMKKTTMKIIPFNRLTIG$_{395}$ (SEQ ID NO: 1) peptide blocks fibrin binding to Mac-1 (29). The γ$^{377-395}$ is a cryptic epitope in the fibrinogen molecule and is exposed only when fibrinogen is immobilized or converted to fibrin (25, 36). We used 200 μM of peptide, a concentration shown to inhibit adhesion of Mac-1 overexpressing cells to immobilized fibrinogen (37), to examine whether the γ$^{377-395}$ peptide could inhibit microglia activation. Fibrinogen treatment resulted in 71±4.9% of activated microglia, when compared to 38.3±9.8% after addition of the γ$^{377-395}$ peptide (P<0.05) (FIGS. 20-21), suggesting that the γ$^{377-395}$ peptide reduced fibrin-mediated microglia activation. The γ$^{377-395}$ peptide did not affect the activation state of untreated microglia and did not inhibit LPS-mediated microglia activation (FIG. 21), further suggesting the specificity of γ$^{377-395}$ to block activation of Mac-1 by fibrin. In accordance, examination of Akt phosphorylation showed that the γ$^{377-395}$ peptide could specifically inhibit fibrin-mediated and not LPS-mediated phosphorylation of Akt (FIG. 22). Overall, these results suggest that inhibition of fibrin/Mac-1 interactions by the γ$^{377-395}$ peptide inhibits both the morphological activation and the signaling cascade induced by fibrin-mediated activation of the Mac-1 microglia receptor.

Example 8

This example illustrates that prophylactic or therapeutic administration of the fibrin γ$^{377-395}$ peptide suppresses EAE and inhibits microglia activation in vivo. Since genetic studies showed that the γ$^{377-395}$ binding epitope of fibrinogen to Mac-1 is not involved in coagulation (15), but is sufficient to inhibit fibrin-mediated microglia activation (FIGS. 14-22), we examined whether blocking exclusively the inflammatory properties of fibrinogen in vivo using the γ$^{377-395}$ would be sufficient to ameliorate EAE. We therefore examined the effects of in vivo administration of the γ$^{377-395}$ fibrin peptide on microglia activation and clinical progression in an animal model for MS. We first assessed the effects of vaccination against γ$^{377-395}$ peptide. Vaccination with γ$^{377-395}$ peptide before the induction of EAE resulted in a significant reduction in disease penetrance and clinical symptoms. All control mice (15/15) developed clinical symptoms of EAE. By contrast, only 53% of the vaccinated mice (8/15) developed EAE. Moreover, mice vaccinated with the γ$^{377-395}$ peptide showed an average clinical score of 1.1, while the control group showed a score of 2.5 (FIG. 23, P<0.01). In a rotarod test, vaccinated mice showed a 76% increase in motor strength and coordination, when compared to the control mice. Quantitative histopathological analysis showed reduced pathology in the brain (index of 1.5±2 vs. 2.3±1) and spinal cord (index of 6.5±5.9 vs. 12±5.2) from γ$^{377-395}$ peptide vaccinated mice as compared to control mice.

Since vaccination is a preventive treatment, we further assessed whether γ$^{377-395}$ peptide would be beneficial if administered after the onset of disease. We administered intranasally (i.n.) 30 μg of γ$^{377-395}$ peptide daily after the first paralytic episode in remitting relapsing EAE (35). Intranasal delivery is a non-invasive delivery method, and results in a higher degree of drug delivery to the nervous system and in a lower degree of systemic drug delivery to tissues such as liver and lymph nodes, when compared to intravenous (i.v.) delivery (38). Intranasal delivery has been previously shown to be effective as a method of drug delivery in EAE (39-41). γ$^{377-395}$ peptide treated mice (n=14) in contrast to control mice (n=13) did not relapse (FIG. 24). Peptide treated mice showed a 1.4-fold increase of motor functions when compared to the control mice after the first relapse on day 29.

Immunohistochemical analysis using Mac-3, a microglia/macrophage marker, revealed reduction of activated cells in the peptide-treated (FIG. 26), as compared to control animals (FIG. 25). In addition, iNOS, a major product of activated CD11b-positive microglia in EAE (42), was reduced in the γ$^{377-395}$ peptide-treated animals (FIG. 26, inset). Quantification of the histopathological analysis shows reduction in both Mac-3 and iNOS, while there are no major differences in T cell infiltrates (FIG. 27). We further examined whether the γ$^{377-395}$ peptide affected the peripheral immune response. FACS analysis on splenocytes of mice immunized with PLP$_{139-151}$ using six markers for peripheral immune cells, namely CD4 and CD8 T cells, CD11b macrophages, CD11c dendritic cells, and CD19 and B220 B cells, did not reveal any differences between untreated and γ$^{377-395}$ peptide treated animals (FIG. 35), suggesting that similar to systemic fibrin depletion (FIG. 34) the γ$^{377-395}$ peptide does not affect the peripheral immune response. These results are in accordance with prior studies where depletion of macrophages (43) or microglia (3) resulted in dramatic reduction of clinical symptoms in EAE even in the presence of functional T cells.

Example 9

This example illustrates that fibrin γ$^{377-395}$ peptide does not affect the coagulation properties of fibrinogen. Several studies have demonstrated both in vivo and in vitro that fibrinogen interacts with different cellular receptors via non overlapping epitopes (for review see (16)). Fibrinogen regulates blood coagulation by engaging the platelet α$_{11b}$β$_3$ integrin receptor via its γ$^{408-411}$ epitope, while it mediates inflammatory processes by engaging the Mac-1 receptor via its γ$^{377-395}$ epitope. As a result fibrinogen knock-in mice, where the γ$^{390-396}$ Mac-1 binding site has'been mutated show normal coagulation properties, such as platelet aggregation, thrombus formation and clotting time (15). To determine whether the γ$^{377-395}$ peptide interfered with blood coagulation, we examined its effects on the coagulative properties of fibrinogen both in vivo and in vitro. As expected, the γ$^{377-395}$ peptide does not affect coagulation in mice (FIG. 28) or prothrombin time (FIG. 29). Moreover, in an in vitro fibrin polymerization assay the γ$^{377-395}$ peptide did not alter the polymerization time of fibrin (FIG. 30). By contrast, the GPRP peptide, an established inhibitor of clot formation (44), inhibits fibrin polymerization (FIG. 30). Overall, these results show that in vivo delivery of the γ377-395 peptide reduces the progression and severity of EAE by specifically targeting microglia/macrophage activation in the CNS parenchyma without adverse hemorrhagic effects.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention. Publications incorporated herein by reference in their entirety include:

1. Lassmann, H., W. Bruck, and C. Lucchinetti 2001. Heterogeneity of multiple sclerosis pathogenesis: implications for diagnosis and therapy. Trends Mol Med 7:115-121.
2. Platten, M., and L. Steinman. 2005. Multiple sclerosis: trapped in deadly glue. Nat Med 11:252-253.
3. Heppner, F. L., M. Greter, D. Marino, J. Falsig, G. Raivich, N. Hovelmeyer, A. Waisman, T. Rulicke, M. Prinz, J. Priller, B. Becher, and A. Aguzzi. 2005. Experimental autoimmune encephalomyelitis repressed by microglial paralysis. Nat Med 11:146-152.
4. Jack, C., F. Ruffini, A. Bar-Or, and J. P. Antel. 2005. Microglia and multiple sclerosis. J Neurosci Res 81:363-373.
5. Minagar, A., and J. S. Alexander. 2003. Blood-brain barrier disruption in multiple sclerosis. Mult Scler 9:540-549.
6. Kermode, A. G., A. J. Thompson, P. Tofts, D. G. MacManus, B. E. Kendall, D. P. Kingsley, I. F. Moseley, P. Rudge, and W. I. McDonald. 1990. Breakdown of the blood-brain barrier precedes symptoms and other MRI signs of new lesions in multiple sclerosis. Pathogenetic and clinical implications. Brain 113:1477-1489.
7. Nimmerjahn, A., F. Kirchhoff, and F. Helmchen. 2005. Resting Microglial Cells Are Highly Dynamic Surveillants of Brain Parenchyma in Vivo. Science 308:1314-1318.
8. Claudio, L., C. S. Raine, and C. F. Brosnan. 1995. Evidence of persistent blood-brain barrier abnormalities in chronic-progressive multiple sclerosis. Acta Neuropathol 90:228-238.
9. Kwon, E. E., and J. W. Prineas. 1994. Blood-brain barrier abnormalities in longstanding multiple sclerosis lesions. An immunohistochemical study. J Neuropathol Exp Neurol 53:625-636.
10. Wakefield, A. J., L. J. More, J. Difford, and J. E. McLaughlin. 1994. Immunohistochemical study of vascular injury in acute multiple sclerosis. J Clin Pathol 47:129-133.
11. Gay, F. W., T. J. Drye, G. W. Dick, and M. M. Esiri. 1997. The application of multifactorial cluster analysis in the staging of plaques in early multiple sclerosis. Identification and characterization of the primary demyelinating lesion. Brain 120 (Pt 8):146'-1483.
12. Tang, L., T. P. Ugarova, E. F. Plow, and J. W. Eaton. 1996. Molecular determinants of acute inflammatory responses to biomaterials. J Clin Invest 97:1329-1334.
13. Languino, L. R., J. Plescia, A. Duperray, A. A. Brian, E. F. Plow, J. E. Geltosky, and D. C. Altieri. 1993. Fibrinogen mediates leukocyte adhesion to vascular endothelium through an ICAM-1-dependent pathway. Cell 73:1423-1434.
14. Herwald, H., H. Cramer, M. Morgelin, W. Russell, U. Sollenberg, A. Norrby Teglund, H. Flodgaard, L. Lindbom, and L. Bjorck. 2004. M Protein, a Classical Bacterial Virulence Determinant, Forms Complexes with Fibrinogen that Induce Vascular Leakage. Cell 116:367-379.
15. Flick, M. J., X. Du, D. P. Witte, M. Jirouskova, D. A. Soloviev, S. J. Busuttil, E. F. Plow, and J. L. Degen. 2004. Leukocyte engagement of fibrin(ogen) via the integrin receptor alphaMbeta2/Mac-1 is critical for host inflammatory response in vivo. J Clin Invest 113:1596-1606.
16. Adams, R. A., M. Passino, B. D. Sachs, T. Nuriel, and K. Akassoglou. 2004. Fibrin mechanisms and functions in nervous system pathology. Mol Interv 4:163-176.
17. Flick, M. J., X. Du, and J. L. Degen. 2004. Fibrin(ogen)-alpha M beta 2 interactions regulate leukocyte function and innate immunity in vivo. Exp Biol Med (Maywood) 229: 1105-1110.
18. Akassoglou, K., R. A. Adams, J. Bauer, V. Tseveleki, P. Mercado, H. Lassmann, L. Probed, and S. Strickland. 2004. Fibrin depletion decreases inflammation and delays the onset of demyelination in a tumor necrosis factor transgenic mouse model for multiple sclerosis. Proc Natl Acad Sci USA 101:6698-6703.
19. Paterson, P. Y. 1976. Experimental allergic encephalomyelitis: role of fibrin deposition in immunopathogenesis of inflammation in rats. Fed Proc 35:2428-2434. [0193]
20. Colder, B. S. 1997. Platelet GPIIb/IIIa antagonists: the first anti-integrin receptor therapeutics. J Clin Invest 99:1467-1471.
21. Rotshenker, S. 2003. Microglia and macrophage activation and the regulation of complement-receptor-3 (CR3/MAC-1)-mediated myelin phagocytosis in injury and disease. J Mol Neurosci 21:65-72.
22. van der Laan, L. J., S. R. Ruuls, K. S. Weber, I. J. Lodder, E. A. Dopp, and C. D. Dijkstra. 1996. Macrophage phagocytosis of myelin in vitro determined by flow cytometry: phagocytosis is mediated by CR3 and induces production of tumor necrosis factor-alpha and nitric oxide. J Neuroimmunol 70:145-152.
23. Reichert, F., U. Slobodov, C. Makranz, and S. Rotshenker. 2001. Modulation (inhibition and augmentation) of complement receptor-3-mediated myelin phagocytosis. Neurobiol Dis 8:504-512.
24. Altieri, D. C., R. Bader, P. M. Mannucci, and T. S. Edgington. 1988. Oligospecificity of the cellular adhesion receptor Mac-1 encompasses an inducible recognition specificity for fibrinogen. J Cell Biol 107:1893-1900.
25. Lishko, V. K., B. Kudryk, V. P. Yakubenko, V. C. Yee, and T. P. Ugarova. 2002. Regulated unmasking of the cryptic binding site for integrin alpha M beta 2 in the gamma C-domain of fibrinogen. Biochemistry 41:12942-12951.
26. Fenteany, G., and M. Glogauer. 2004. Cytoskeletal remodeling in leukocyte function. Curr Opin Hematol 11:15-24.

27. Harrison, R. E., and S. Grinstein. 2002. Phagocytosis and the microtubule cytoskeleton. Biochem Cell Biol 80:509-515.
28. Ehlers, M. R. W. 2000. CR3: a general purpose adhesion recognition receptor essential for innate immunity. Microbes and Infection 2:289-294.
29. Ugarova, T. P., D. A. Solovjov, L. Zhang, D. I. Loukinov, V. C. Yee, L. V. Medved, and E. F. Plow. 1998. Identification of a novel recognition sequence for integrin alphaM beta2 within the gamma-chain of fibrinogen. J Biol Chem 273:22519-22527.
30. Lehnardt, S., L. Massillon, P. Follett, F. E. Jensen, R. Ratan, P. A. Rosenberg, J. J. Volpe, and T. Vartanian. 2003. Activation of innate immunity in the CNS triggers neurodegeneration through a Toll-like receptor 4-dependent pathway. Proc Natl Acad Sci USA 100:8514-8519.
31. Lehnardt, S., C. Lachance, S. Patrizi, S. Lefebvre, P. L. Follett, F. E. Jensen, P. A. Rosenberg, J. J. Volpe, and T. Vartanian. 2002. The toll-like receptor TLR4 is necessary for lipopolysaccharide-induced oligodendrocyte injury in the CNS. J Neurosci 22:2478-2486.
32. Stephens, L., C. Ellson, and P. Hawkins. 2002. Roles of PI3Ks in leukocyte chemotaxis and phagocytosis. Curr Opin Cell Biol 14:203-213.
33. Caron, E., and A. Hall. 1998. Identification of two distinct mechanisms of phagocytosis controlled by different Rho GTPases. Science 282:1717-1721.
34. Bell, W. R., S. S. Shapiro, J. Martinez, and H. L. Nossel. 1978. The effects of ancrod, the coagulating enzyme from the venom of Malayan pit viper (A. rhodostoma) on prothrombin and fibrinogen metabolism and fibrinopeptide A release in man. J Lab Clin Med 91:592-604.
35. Youssef, S., O. Stuve, J. C. Patarroyo, P. J. Ruiz, J. L. Radosevich, E. M. Hur, M. Bravo, D. J. Mitchell, R. A. Sobel, L. Steinman, and S. S. Zamvil. 2002. The HMG CoA reductase inhibitor, atorvastatin, promotes a Th2 bias and reverses paralysis in central nervous system autoimmune disease. Nature 420:78-84.
36. Ugarova, T. P., and V. P. Yakubenko. 2001. Recognition of fibrinogen by leukocyte integrins. Ann NY Acad Sci 936:368-385.
37. Ugarova, T. P., V. K. Lishko, N. P. Podolnikova, N. Okumura, S. M. Merkulov, V. P. Yakubenko, V. C. Yee, S. T. Lord, and T. A. Haas. 2003. Sequence gamma 377 395(P2), but not gamma 190-202(P1), is the binding site for the alpha MI-domain of integrin alpha M beta 2 in the gamma C-domain of fibrinogen. Biochemistry 42:93659373.
38. Ross, T. M., P. M. Martinez, J. C. Renner, R. G. Thorne, L. R. Hanson, and W. H. Frey, 2nd. 2004. Intranasal administration of interferon beta bypasses the blood-brain barrier to target the central nervous system and cervical lymph nodes: a non-invasive treatment strategy for multiple sclerosis. J Neuroimmunol 151:66-77.
39. Yura, M., I. Takahashi, S. Terawaki, T. Hiroi, M. N. Kweon, Y. Yuki, and H. Kiyono. 2001. Nasal administration of cholera toxin (CT) suppresses clinical signs of experimental autoimmune encephalomyelitis (EAE). Vaccine 20:134139.
40. Xiao, B. G., X. F. Bai, G. X. Zhang, and H. Link. 1998. Suppression of acute and protracted-relapsing experimental allergic encephalomyelitis by nasal administration of low-dose IL-10 in rats. J Neuroimmunol 84:230-237.
41. Ishikawa, M., Y. Jin, H. Guo, H. Link, and B. G. Xiao. 1999. Nasal administration of transforming growth factor-beta1 induces dendritic cells and inhibits protracted relapsing experimental allergic encephalomyelitis. Mult Scler 5:184-191.
42. Tran, E. H., H. Hardin-Pouzet, G. Verge, and T. Owens. 1997. Astrocytes and microglia express inducible nitric oxide synthase in mice with experimental allergic encephalomyelitis. J Neuroimmunol 74:121-129.
43. Brosnan, C. F., M. B. Bornstein, and B. R. Bloom. 1981. The effects of macrophage depletion on the clinical and pathologic expression of experimental allergic encephalomyelitis. J Immunol 126:614-620.
44. Laudano, A. P., and R. F. Doolittle. 1981. Influence of calcium ion on the binding of fibrin amino terminal peptides to fibrinogen. Science 212:457-459.
45. Vos, C. M., J. J. Geurts, L. Montagne, E. S. van Haastert, L. Bo, P. van der Valk, F. Barkhof, and H. E. de Vries. 2005. Blood-brain barrier alterations in both focal and diffuse abnormalities on postmortem MRI in multiple sclerosis. Neurobiol Dis 20:953-960.
46. Monje, M. L., H. Toda, and T. D. Palmer. 2003. Inflammatory blockade restores adult hippocampal neurogenesis. Science 302:1760-1765.
47. Inoue, A., C. S. Koh, K. Shimada, N. Yanagisawa, and K. Yoshimura. 1996. Suppression of cell-transferred experimental autoimmune encephalomyelitis in defibrinated Lewis rats. J Neuroimmunol 71:131-137.
48. Loike, J. D., B. Sodeik, L. Cao, S. Leucona, J. I. Weitz, P. A. Detmers, S. D. Wright, and S. C. Silverstein. 1991. CD11c/CD18 on neutrophils recognizes a domain at the N terminus of the A alpha chain of fibrinogen. Proc Natl Acad Sci USA 88:1044-1048.
49. McMahon, E. J., S. L. Bailey, C. V. Castenada, H. Waldner, and S. D. Miller. 2005. Epitope spreading initiates in the CNS in two mouse models of multiple sclerosis. Nat Med 11:335-339.
50. Greter, M., F. L. Heppner, M. P. Lemos, B. M. Odermatt, N. Goebels, T. Laufer, R. J. Noelle, and B. Becher. 2005. Dendritic cells permit immune invasion of the CNS in an animal model of multiple sclerosis. Nat Med 11:328-334.
51. Carson, M. J. 2002. Microglia as liaisons between the immune and central nervous systems: functional implications for multiple sclerosis. Glia 40:218-231.
52. Lucchinetti, C. F., W. Bruck, M. Rodriguez, and H. Lassmann. 1996. Distinct patterns of multiple sclerosis pathology indicates heterogeneity on pathogenesis. Brain Pathol 6:259-274.
53. Barnett, M. H., A. P. Henderson, and J. W. Prineas. 2006. The macrophage in MS: just a scavenger after all? Pathology and pathogenesis of the acute MS lesion. Mult Scler 12:121-132.
54. Noseworthy, J., D. Miller, and A. Compston. 2006. Disease-modifying treatments in multiple sclerosis. McAlpine's Multiple Sclerosis, Churchill Livingstone, Elsevier, Philadelphia, Pa. 729-802 pp.
55. Akassoglou, K., W.-M. Yu, P. Akpinar, and S. Strickland. 2002. Fibrin inhibits peripheral nerve regeneration by arresting Schwann cell differentiation. Neuron 33:861-875.
56. Karnezis, T., W. Mandemakers, J. L. McQualter, B. Zheng, P. P. Ho, K. A. Jordan, B. M. Murray, B. Barres, M. Tessier-Lavigne, and C. C. Bernard. 2004. The neurite outgrowth inhibitor Nogo A is involved in autoimmune-mediated demyelination. Nat Neurosci 7:736-744.
57. Akassoglou, K., J. Bauer, G. Kassiotis, M. Pasparakis, H. Lassmann, G. Kollias, and L. Probert. 1998. Oligodendrocyte apoptosis and primary demyelination induced by local TNF/p55TNF receptor signaling in the central nervous system of transgenic mice: models for multiple sclerosis with primary oligodendrogliopathy. Am J Pathol 153:801-813.
58. Akassoglou, K., B. Malester, J. Xu, L. Tessarollo, J. Rosenbluth, and M. V. Chao. 2004. Brain-specific deletion of neuropathy target esterase/swisscheese results in neurodegeneration. Proc Natl Acad Sci USA 101:5075-5080.
59. Siao, C. J., S. R. Fernandez, and S. E. Tsirka. 2003. Cell type-specific roles for tissue plasminogen activator released by neurons or microglia after excitotoxic injury. J Neurosci 23:3234-3242.
60. Seasholtz, T. M., J. Radeff-Huang, S. A. Sagi, R. Matteo, J. M. Weems, A. S. Cohen, J. R. Feramisco, and J. H. Brown. 2004. Rho-mediated cytoskeletal rearrangement in response to LPA is functionally antagonized by Rac1 and PIP2. J Neurochem 91:501 512.

What is claimed is:

1. A method for the treatment of a degenerative disorder of the nervous system comprising administering to a subject in need an effective amount of a composition comprising a pharmaceutically acceptable excipient and an antibody that binds a peptide consisting of an amino acid sequence at least 89% identical to SEQ ID NO: 1, wherein said antibody inhibits fibrin γ377-395 (SEQ ID NO:1) specific binding to Mac-1, wherein the degenerative disorder of the nervous system involves leakage of fibrinogen perivascularly in the brain.

2. The method of claim 1, wherein the antibody is a monoclonal antibody.

3. The method of claim 1, wherein the antibody is an antigen-binding fragment selected from the group consisting of Fab, Fab', F(ab')$_2$ and F(v).

4. The method of claim 1, wherein the antibody is chimeric.

5. The method of claim 1, wherein the antibody is humanized.

6. The method of claim 1, wherein the degenerative disorder of the nervous system is selected from the group consisting of multiple sclerosis, spinal cord injury, stroke and Alzheimer's Disease.

7. The method of claim 1, wherein the amino acid sequence is at least 94% identical to SEQ ID NO:1.

8. The method of claim 1, wherein the amino acid sequence is shown in SEQ ID NO:1.

9. The method of claim 1, wherein the antibody is a human antibody.

* * * * *

UNITED STATES PATENT AND TRADEMARK OFFICE
CERTIFICATE OF CORRECTION

PATENT NO. : 8,569,242 B2
APPLICATION NO. : 13/337504
DATED : October 29, 2013
INVENTOR(S) : Katerina Akassoglou It is certified that error appears in the above-identified patent and that said Letters Patent is hereby corrected as shown below:

On the Title page, at item (60) Provisional application No., delete "60/702,218" and insert --60/720,218--.

Signed and Sealed this
Tenth Day of December, 2013

Margaret A. Focarino
*Commissioner for Patents of the United States Patent and Trademark Office*

SEQUENCE LISTING

```
<160> NUMBER OF SEQ ID NOS: 6

<210> SEQ ID NO 1
<211> LENGTH: 19
<212> TYPE: PRT
<213> ORGANISM: Homo sapiens

<400> SEQUENCE: 1

Tyr Ser Met Lys Lys Thr Thr Met Lys Ile Ile Pro Phe Asn Arg Leu
1               5                   10                  15

Thr Ile Gly

<210> SEQ ID NO 2
<211> LENGTH: 19
<212> TYPE: PRT
<213> ORGANISM: Homo sapiens

<400> SEQUENCE: 2

Tyr Ser Met Lys Glu Thr Thr Met Lys Ile Ile Pro Phe Asn Arg Leu
1               5                   10                  15

Ser Ile Gly

<210> SEQ ID NO 3
<211> LENGTH: 7
<212> TYPE: PRT
<213> ORGANISM: Homo sapiens

<400> SEQUENCE: 3

Asn Arg Leu Ser Ile Gly Glu
1               5

<210> SEQ ID NO 4
<211> LENGTH: 7
<212> TYPE: PRT
<213> ORGANISM: Homo sapiens

<400> SEQUENCE: 4

Ala Ala Ala Ala Ala Ala Ala
1               5

<210> SEQ ID NO 5
<211> LENGTH: 13
<212> TYPE: PRT
<213> ORGANISM: Unknown
<220> FEATURE:
<223> OTHER INFORMATION: Description of Unknown: Proteolipid
      peptide

<400> SEQUENCE: 5

His Ser Leu Gly Lys Trp Leu Gly His Pro Asp Lys Phe
1               5                   10

<210> SEQ ID NO 6
<211> LENGTH: 21
```

```
<212> TYPE: PRT
<213> ORGANISM: Unknown
<220> FEATURE:
<223> OTHER INFORMATION: Description of Unknown: Myelin oligodendrocyte
      glycoprotein peptide

<400> SEQUENCE: 6

Met Glu Val Gly Trp Tyr Arg Ser Pro Phe Ser Arg Val Val His Leu
1               5                   10                  15

Tyr Arg Asp Gly Lys
            20
```